(12) United States Patent  
Kubota et al.

(10) Patent No.: US 11,684,254 B2  
(45) Date of Patent: *Jun. 27, 2023

(54) SCAN PATTERN AND SIGNAL PROCESSING FOR OPTICAL COHERENCE TOMOGRAPHY

(71) Applicant: ACUCELA INC., Seattle, WA (US)

(72) Inventors: Ryo Kubota, Seattle, WA (US); Stephan Wyder, Bern (CH); Philip M. Buscemi, Mount Pleasant, SC (US); Matthias Pfister, Bern (CH); Alexander Holzer, Bern (CH)

(73) Assignee: ACUCELA INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/662,582

(22) Filed: May 9, 2022

(65) Prior Publication Data

US 2022/0257112 A1 Aug. 18, 2022

Related U.S. Application Data

(63) Continuation of application No. 17/248,870, filed on Feb. 11, 2021, now Pat. No. 11,369,266, which is a (Continued)

(51) Int. Cl.
*A61B 3/10* (2006.01)
*G01B 9/02004* (2022.01)
(Continued)

(52) U.S. Cl.
CPC ............ *A61B 3/102* (2013.01); *A61B 3/1225* (2013.01); *G01B 9/02004* (2013.01); *G01B 9/02091* (2013.01)

(58) Field of Classification Search
CPC ........... A61B 3/10; A61B 3/102; A61B 3/103; A61B 3/1015; A61B 3/12; A61B 3/1225;
(Continued)

(56) References Cited

U.S. PATENT DOCUMENTS 5,255,274 A 10/1993 Wysocki
5,396,325 A 3/1995 Carome
(Continued)

FOREIGN PATENT DOCUMENTS

CA 3111012 1/2021
CN 105188540 12/2015
(Continued)

OTHER PUBLICATIONS

Bengio, Yoshua, et al., "Curriculum Learning," 8 pages, retrieved from http://machinelearning.org/archive/icml2009/papers/119.pdf on Jun. 14, 2021.
(Continued)

*Primary Examiner* — Jie Lei
(74) *Attorney, Agent, or Firm* — Fisherbroyles LLP; John Shimmick

(57) ABSTRACT

An OCT system for measuring a retina as part of an eye health monitoring and diagnosis system. The OCT system includes an OCT interferometer, where the interferometer comprises a light source or measurement beam and a scanner for moving the beam on the retina of a patient's eye, and a processor configured to execute instructions to cause the scanner to move the measurement beam on the retina in a scan pattern. The scan pattern is a continuous pattern that includes a plurality of lobes. The measurement beam may be caused to move on the retina by the motion of a mirror that intercepts and redirects the measurement beam. The mirror position may be altered by the application of a drive signal to one or more actuators that respond to the drive signal by rotating the mirror about an axis or axes.

14 Claims, 18 Drawing Sheets

Related U.S. Application Data continuation of application No. 16/947,728, filed on Aug. 13, 2020, now Pat. No. 10,959,613.

(60) Provisional application No. 62/706,193, filed on Aug. 4, 2020.

(51) Int. Cl.
*G01B 9/02091* (2022.01)
*A61B 3/12* (2006.01)

(58) Field of Classification Search
CPC .... A61B 3/113; A61B 3/14; A61B 3/152; A61B 5/0059; A61B 5/0066; G01B 9/02; G01B 9/02004; G01B 9/02091; G01B 9/02077; G01B 9/02051; G01B 9/02074; G01B 2290/65
USPC ....... 351/205, 206, 208, 210–212, 221, 236, 351/246
See application file for complete search history.

(56) References Cited

U.S. PATENT DOCUMENTS

| | | | |
|---|---|---|---|
| 6,053,613 | A | 4/2000 | Wei |
| 6,325,512 | B1 | 12/2001 | Wei |
| 6,362,919 | B1 | 3/2002 | Flanders |
| 6,409,395 | B1 | 6/2002 | Wang |
| 6,419,360 | B1 | 7/2002 | Hauger |
| 6,445,944 | B1 | 9/2002 | Ostrovsky |
| 6,552,796 | B2 | 4/2003 | Magnin |
| 6,726,325 | B2 | 4/2004 | Xie |
| 6,736,508 | B2 | 5/2004 | Xie |
| 6,769,769 | B2 | 8/2004 | Podoleanu |
| 6,778,307 | B2 | 8/2004 | Clark |
| 7,113,818 | B2 | 9/2006 | Podoleanu |
| 7,126,693 | B2 | 10/2006 | Everett |
| 7,140,730 | B2 | 11/2006 | Wei |
| 7,301,644 | B2 | 11/2007 | Knighton |
| 7,324,569 | B2 | 1/2008 | Flanders |
| 7,347,548 | B2 | 3/2008 | Huang |
| 7,375,818 | B2 | 5/2008 | Kawahara |
| 7,391,520 | B2 | 6/2008 | Zhou |
| 7,452,077 | B2 | 11/2008 | Meyer |
| 7,482,589 | B2 | 1/2009 | Flanders |
| 7,542,145 | B2 | 6/2009 | Toida |
| 7,594,730 | B2 | 9/2009 | Podoleanu |
| 7,602,500 | B2 | 10/2009 | Izatt |
| 7,633,623 | B2 | 12/2009 | Hatori |
| 7,633,627 | B2 | 12/2009 | Choma |
| 7,701,585 | B2 | 4/2010 | Hatori |
| 7,761,139 | B2 | 7/2010 | Tearney |
| 7,783,337 | B2 | 8/2010 | Feldman |
| 7,864,335 | B2 | 1/2011 | Terakawa |
| 7,872,759 | B2 | 1/2011 | Tearney |
| 7,929,148 | B2 | 4/2011 | Kemp |
| 7,954,947 | B2 | 6/2011 | Sugita |
| 7,971,999 | B2 | 7/2011 | Zinser |
| 7,980,694 | B2 | 7/2011 | Keating |
| 7,980,696 | B1 | 7/2011 | Taki |
| 7,997,728 | B2 | 8/2011 | Huang |
| 7,997,729 | B2 | 8/2011 | Mclean |
| 8,025,403 | B2 | 9/2011 | Maloca |
| 8,049,900 | B2 | 11/2011 | Kemp |
| 8,055,107 | B2 | 11/2011 | Masuda |
| 8,079,711 | B2 | 12/2011 | Stetson |
| 8,123,354 | B2 | 2/2012 | Olivier |
| 8,139,226 | B2 | 3/2012 | Johnson |
| 8,192,024 | B2 | 6/2012 | Yumikake |
| 8,205,991 | B2 | 6/2012 | Wei |
| 8,220,924 | B2 | 7/2012 | Hanebuchi |
| 8,251,510 | B2 | 8/2012 | Kobayashi |
| 8,251,511 | B2 | 8/2012 | Stetson |
| 8,282,211 | B2 | 10/2012 | Campbell |
| 8,289,522 | B2 | 10/2012 | Tearney |
| 8,348,427 | B2 | 1/2013 | Buckland |
| 8,348,429 | B2 | 1/2013 | Walsh |
| 8,351,665 | B2 | 1/2013 | Tearney |
| 8,363,783 | B2 | 1/2013 | Gertner |
| 8,403,481 | B2 | 3/2013 | Izatt |
| 8,405,834 | B2 | 3/2013 | Srinivasan |
| 8,421,855 | B2 | 4/2013 | Buckland |
| 8,425,037 | B2 | 4/2013 | Uhlhorn |
| 8,442,284 | B2 | 5/2013 | Rogers |
| 8,446,593 | B1 | 5/2013 | Ellerbee |
| 8,457,440 | B1 | 6/2013 | Johnson |
| 8,467,051 | B2 | 6/2013 | Flanders |
| 8,474,978 | B2 | 7/2013 | Huang |
| 8,500,279 | B2 | 8/2013 | Everett |
| 8,526,006 | B2 | 9/2013 | Nebosis |
| 8,529,062 | B2 | 9/2013 | Buckland |
| 8,594,757 | B2 | 11/2013 | Boppart |
| 8,608,314 | B2 | 12/2013 | Yoon |
| 8,630,697 | B2 | 1/2014 | Meyer |
| 8,665,450 | B2 | 3/2014 | Johnson |
| 8,711,366 | B2 | 4/2014 | Everett |
| 8,721,078 | B2 | 5/2014 | Torii |
| 8,724,870 | B2 | 5/2014 | Sekine |
| 8,757,803 | B2 | 6/2014 | Everett |
| 8,781,287 | B2 | 7/2014 | Flanders |
| 8,794,763 | B2 | 8/2014 | Stetson |
| 8,801,184 | B2 | 8/2014 | Hacker |
| 8,820,931 | B2 | 9/2014 | Walsh |
| 8,836,953 | B2 | 9/2014 | Johnson |
| 8,870,376 | B2 | 10/2014 | Hogan |
| 8,894,207 | B2 | 11/2014 | Hee |
| 8,913,248 | B2 | 12/2014 | Sharma |
| 8,922,782 | B2 | 12/2014 | Flanders |
| 8,926,097 | B2 | 1/2015 | Sakagawa |
| 8,939,582 | B1 | 1/2015 | Spaide |
| 8,947,648 | B2 | 2/2015 | Swanson |
| 8,953,167 | B2 | 2/2015 | Johnson |
| 8,971,360 | B2 | 3/2015 | Lewandowski |
| 8,992,018 | B2 | 3/2015 | Makihira |
| 8,994,753 | B2 | 3/2015 | Nakano |
| 8,998,412 | B2 | 4/2015 | Makihira |
| 9,016,862 | B2 | 4/2015 | Carnevale |
| 9,025,160 | B2 | 5/2015 | Moore |
| 9,025,847 | B2 | 5/2015 | Kitamura |
| 9,033,504 | B2 | 5/2015 | Everett |
| 9,033,510 | B2 | 5/2015 | Narasimha-Iyer |
| 9,044,164 | B2 | 6/2015 | Hacker |
| 9,055,891 | B2 | 6/2015 | Suehira |
| 9,055,892 | B2 | 6/2015 | Narasimha-Iyer |
| 9,060,689 | B2 | 6/2015 | Tearney |
| 9,084,562 | B2 | 7/2015 | Kakuma |
| 9,095,281 | B2 | 8/2015 | Sharma |
| 9,119,562 | B2 | 9/2015 | Naba |
| 9,138,141 | B2 | 9/2015 | Makihira |
| 9,144,378 | B2 | 9/2015 | Suehira |
| 9,149,182 | B2 | 10/2015 | Walsh |
| 9,161,690 | B2 | 10/2015 | Tomatsu |
| 9,163,929 | B2 | 10/2015 | Lim |
| 9,163,930 | B2 | 10/2015 | Buckland |
| 9,167,964 | B2 | 10/2015 | Everett |
| 9,171,367 | B2 | 10/2015 | Iwase |
| 9,176,319 | B2 | 11/2015 | Bouma |
| 9,178,330 | B2 | 11/2015 | Oh |
| 9,192,294 | B2 | 11/2015 | Sharma |
| 9,200,888 | B2 | 12/2015 | Jaillon |
| 9,217,707 | B2 | 12/2015 | Bajraszewski |
| 9,226,653 | B2 | 1/2016 | Torii |
| 9,226,660 | B2 | 1/2016 | De Boer |
| 9,241,626 | B2 | 1/2016 | Narasimha-Iyer |
| 9,243,885 | B2 | 1/2016 | Johnson |
| 9,259,151 | B2 | 2/2016 | Murase |
| 9,267,783 | B1 | 2/2016 | Sharma |
| 9,273,950 | B2 | 3/2016 | Yazdanfar |
| 9,291,446 | B2 | 3/2016 | Schneider |
| 9,310,182 | B2 | 4/2016 | Goldberg |
| 9,339,186 | B2 | 5/2016 | Somani |
| 9,354,038 | B2 | 5/2016 | Yasuno |
| 9,373,933 | B2 | 6/2016 | Njegovec |
| 9,375,158 | B2 | 6/2016 | Vakoc |

(56) References Cited

U.S. PATENT DOCUMENTS

| | | |
|---|---|---|
| 9,377,293 B2 | 6/2016 | Hauger |
| 9,380,935 B2 | 7/2016 | Iwase |
| 9,408,532 B2 | 8/2016 | Makihira |
| 9,427,147 B2 | 8/2016 | Lujan |
| 9,427,150 B2 | 8/2016 | Muto |
| 9,433,353 B2 | 9/2016 | Hanebuchi |
| 9,468,374 B2 | 10/2016 | Makihira |
| 9,492,077 B2 | 11/2016 | Ebersbach |
| 9,492,079 B2 | 11/2016 | Walsh |
| 9,526,412 B2 | 12/2016 | Yang |
| 9,526,415 B2 | 12/2016 | Fukuma |
| 9,526,425 B2 | 12/2016 | Feldman |
| 9,532,713 B2 | 1/2017 | Levecq |
| 9,545,199 B2 | 1/2017 | Wang |
| 9,584,098 B2 | 2/2017 | Yamanari |
| 9,612,105 B2 | 4/2017 | Kemp |
| 9,615,736 B2 | 4/2017 | Yamashita |
| 9,633,424 B2 | 4/2017 | Nebosis |
| 9,649,024 B2 | 5/2017 | Hacker |
| 9,649,025 B2 | 5/2017 | Jeglorz |
| 9,671,620 B2 | 6/2017 | Gupta |
| 9,696,132 B2 | 7/2017 | Jayaraman |
| 9,702,686 B2 | 7/2017 | Hattersley |
| 9,778,018 B2 | 10/2017 | Schmoll |
| 9,778,020 B2 | 10/2017 | Tumlinson |
| 9,784,559 B2 | 10/2017 | Huber |
| 9,812,846 B2 | 11/2017 | Yun |
| 9,869,542 B2 | 1/2018 | Goldberg |
| 9,897,538 B2 | 2/2018 | Tearney |
| 9,915,520 B2 | 3/2018 | Cable |
| 9,939,659 B2 | 4/2018 | Gupta |
| 9,948,061 B2 | 4/2018 | Njegovec |
| 9,977,184 B1 | 5/2018 | Wong |
| 9,978,159 B2 | 5/2018 | Kraus |
| 9,993,153 B2 | 6/2018 | Chong |
| 10,045,692 B2 | 8/2018 | Tumlinson |
| 10,049,470 B2 | 8/2018 | Pintal |
| 10,098,537 B2 | 10/2018 | Iwase |
| 10,114,232 B2 | 10/2018 | Gupta |
| 10,327,631 B2 | 6/2019 | Huang |
| 10,413,175 B2 | 9/2019 | Yun |
| 10,478,058 B2 | 11/2019 | Cheng |
| 10,568,501 B2 | 2/2020 | Boss |
| 10,595,723 B2 | 3/2020 | Meznaric |
| 10,610,096 B2 | 4/2020 | Scheibler |
| 10,912,456 B2 | 2/2021 | Brennan |
| 10,952,607 B2 | 3/2021 | Scheibler |
| 10,959,613 B1* | 3/2021 | Kubota ............. G01B 9/02027 |
| 11,369,266 B2 | 6/2022 | Kubota |
| 11,393,094 B2 | 7/2022 | Wyder |
| 2005/0018133 A1 | 1/2005 | Huang |
| 2005/0140981 A1 | 6/2005 | Waelti |
| 2006/0131488 A1 | 6/2006 | Thingbo |
| 2006/0152106 A1 | 7/2006 | Yan |
| 2006/0244339 A1 | 11/2006 | Mazz |
| 2007/0076217 A1 | 4/2007 | Baker |
| 2007/0183643 A1 | 8/2007 | Jayaraman |
| 2007/0230856 A1 | 10/2007 | Yamazaki |
| 2008/0100612 A1 | 5/2008 | Dastmalchi |
| 2008/0117427 A1 | 5/2008 | Teramura |
| 2008/0181263 A1 | 7/2008 | Bouma |
| 2008/0296480 A1 | 12/2008 | Haber |
| 2009/0123044 A1 | 5/2009 | Huang |
| 2009/0141237 A1 | 6/2009 | Izatt |
| 2010/0110376 A1 | 5/2010 | Everett |
| 2010/0110377 A1 | 5/2010 | Maloca |
| 2011/0043757 A1 | 2/2011 | Everett |
| 2011/0080561 A1 | 4/2011 | Hayashi |
| 2011/0164633 A1 | 7/2011 | Moench |
| 2011/0299034 A1 | 12/2011 | Walsh |
| 2012/0033227 A1 | 2/2012 | Bower |
| 2012/0092616 A1 | 4/2012 | Peyman |
| 2012/0300216 A1 | 11/2012 | Johnson |
| 2012/0327365 A1 | 12/2012 | Makihira |
| 2013/0010259 A1 | 1/2013 | Carnevale |
| 2013/0010302 A1 | 1/2013 | Sharma |
| 2013/0016360 A1 | 1/2013 | Ensher |
| 2013/0103014 A1* | 4/2013 | Gooding ............. A61B 3/0025 606/4 |
| 2013/0158392 A1 | 6/2013 | Papac |
| 2013/0235343 A1 | 9/2013 | Hee |
| 2013/0250241 A1 | 9/2013 | Everett |
| 2014/0028997 A1 | 1/2014 | Cable |
| 2014/0112562 A1 | 4/2014 | Yamakawa |
| 2014/0121508 A1 | 5/2014 | Latimer |
| 2014/0125987 A1 | 5/2014 | Flanders |
| 2014/0218745 A1 | 8/2014 | Hattersley |
| 2014/0241605 A1 | 8/2014 | Izatt |
| 2014/0268050 A1 | 9/2014 | Jayaraman |
| 2014/0268169 A1 | 9/2014 | Jayaraman |
| 2014/0269796 A1 | 9/2014 | Geske |
| 2014/0285812 A1 | 9/2014 | Levitz |
| 2014/0307078 A1 | 10/2014 | Charles |
| 2014/0307753 A1 | 10/2014 | Minneman |
| 2014/0340689 A1 | 11/2014 | Namati |
| 2014/0347632 A1 | 11/2014 | Mordaunt |
| 2015/0010031 A1 | 1/2015 | Makino |
| 2015/0018674 A1 | 1/2015 | Scott |
| 2015/0055089 A1 | 2/2015 | Aono |
| 2015/0062532 A1 | 3/2015 | Sharma |
| 2015/0085253 A1 | 3/2015 | Walsh |
| 2015/0109579 A1 | 4/2015 | Orlowski |
| 2015/0110376 A1 | 4/2015 | Gessner |
| 2015/0198431 A1* | 7/2015 | Uchida ............... H01S 5/18366 372/20 |
| 2015/0216412 A1 | 8/2015 | Hillmann |
| 2015/0327761 A1 | 11/2015 | Narasimha-Iyer |
| 2015/0327762 A1 | 11/2015 | Isogai |
| 2016/0000368 A1 | 1/2016 | Wang |
| 2016/0007857 A1 | 1/2016 | Wang |
| 2016/0025478 A1 | 1/2016 | Johnson |
| 2016/0040976 A1 | 2/2016 | Berkeley |
| 2016/0040977 A1 | 2/2016 | An |
| 2016/0040978 A1 | 2/2016 | Boppart |
| 2016/0081545 A1 | 3/2016 | Hauger |
| 2016/0082129 A1 | 3/2016 | Peters |
| 2016/0106310 A1 | 4/2016 | Moriguchi |
| 2016/0106312 A1 | 4/2016 | Moriguchi |
| 2016/0106314 A1 | 4/2016 | Everett |
| 2016/0128565 A1* | 5/2016 | Meznaric ............... A61B 3/102 351/212 |
| 2016/0166143 A1 | 6/2016 | Goto |
| 2016/0206190 A1 | 7/2016 | Reisman |
| 2016/0242638 A1 | 8/2016 | Durbin |
| 2016/0252340 A1 | 9/2016 | Hollenbeck |
| 2016/0262609 A1 | 9/2016 | Cai |
| 2016/0270656 A1 | 9/2016 | Samec |
| 2016/0321828 A1 | 11/2016 | Tachikawa |
| 2016/0338589 A1 | 11/2016 | Carrasco-Zevallos |
| 2016/0367129 A1 | 12/2016 | Coelho |
| 2016/0367132 A1 | 12/2016 | Yun |
| 2017/0007182 A1 | 1/2017 | Samec |
| 2017/0020387 A1 | 1/2017 | Fingler |
| 2017/0049318 A1 | 2/2017 | Walsh |
| 2017/0055829 A1 | 3/2017 | Tan |
| 2017/0065169 A1 | 3/2017 | Fukasawa |
| 2017/0074640 A1 | 3/2017 | Cable |
| 2017/0102223 A1 | 4/2017 | Izatt |
| 2017/0105618 A1 | 4/2017 | Schmoll |
| 2017/0140560 A1 | 5/2017 | Kraus |
| 2017/0156583 A1 | 6/2017 | Seesselberg |
| 2017/0205223 A1 | 7/2017 | Cable |
| 2017/0227350 A1 | 8/2017 | Sarunic |
| 2017/0231489 A1 | 8/2017 | Fujimori |
| 2017/0241763 A1 | 8/2017 | Wang |
| 2017/0258321 A1 | 9/2017 | Dastmalchi |
| 2017/0268987 A1 | 9/2017 | Swanson |
| 2017/0276471 A1 | 9/2017 | Jiang |
| 2017/0280993 A1 | 10/2017 | Fukuhara |
| 2017/0311795 A1 | 11/2017 | Sumiya |
| 2017/0356740 A1 | 12/2017 | Ansari |
| 2018/0012359 A1 | 1/2018 | Prentasic |
| 2018/0031363 A1 | 2/2018 | Johnson |
| 2018/0051978 A1 | 2/2018 | Flanders |

(56) References Cited

U.S. PATENT DOCUMENTS

| | | |
|---|---|---|
| 2018/0055358 A1 | 3/2018 | Nakajima |
| 2018/0064331 A1 | 3/2018 | Naba |
| 2018/0084994 A1 | 3/2018 | Su |
| 2018/0125354 A1 | 5/2018 | Pulaski |
| 2018/0135962 A1 | 5/2018 | Murata |
| 2018/0156598 A1 | 6/2018 | Cable |
| 2018/0157924 A1 | 6/2018 | Hogan |
| 2018/0168445 A1 | 6/2018 | Horn |
| 2018/0206716 A1 | 7/2018 | Chong |
| 2018/0271363 A1 | 9/2018 | Scheibler |
| 2018/0289256 A1 | 10/2018 | Murata |
| 2019/0365220 A1 | 12/2019 | Frisken |
| 2019/0380574 A1 | 12/2019 | Chen |
| 2020/0093363 A1 | 3/2020 | Saika |
| 2020/0196858 A1 | 6/2020 | Scheibler |
| 2020/0234080 A1 | 7/2020 | Ciller Ruiz |
| 2020/0342595 A1 | 10/2020 | Jia |
| 2020/0372632 A1 | 11/2020 | Chauhan |
| 2021/0127969 A1 | 5/2021 | Oggenfuss |

FOREIGN PATENT DOCUMENTS

| | | |
|---|---|---|
| CN | 105263415 | 1/2016 |
| CN | 105792728 | 7/2016 |
| DE | 102016121246 | 5/2018 |
| EP | 2725508 | 4/2014 |
| EP | 2759254 | 7/2014 |
| EP | 2892413 | 7/2015 |
| JP | 201172716 | 4/2011 |
| JP | 201483266 | 5/2014 |
| JP | 2016514828 | 5/2016 |
| WO | 9320743 | 10/1993 |
| WO | 2009120544 | 10/2009 |
| WO | 2010117386 | 10/2010 |
| WO | 2015082001 | 6/2015 |
| WO | 2015116981 | 8/2015 |
| WO | 2015120055 | 8/2015 |
| WO | 2016040534 | 3/2016 |
| WO | 2016073840 | 5/2016 |
| WO | 2016115387 | 7/2016 |
| WO | 2016125474 | 8/2016 |
| WO | 2016127140 | 8/2016 |
| WO | 2016148569 | 9/2016 |
| WO | 2016178298 | 11/2016 |
| WO | 2016179431 | 11/2016 |
| WO | 2016196463 | 12/2016 |
| WO | 2016203245 | 12/2016 |
| WO | 2017002379 | 1/2017 |
| WO | 2017025583 | 2/2017 |
| WO | 2017046225 | 3/2017 |
| WO | 2017048832 | 3/2017 |
| WO | 2017165793 | 9/2017 |
| WO | 2017176301 | 10/2017 |
| WO | 2017206929 | 12/2017 |
| WO | 2017216242 | 12/2017 |
| WO | 2018086173 | 5/2018 |
| WO | 2018089682 | 5/2018 |
| WO | 2018105549 | 6/2018 |
| WO | 2018116128 | 6/2018 |
| WO | 2018119077 | 6/2018 |
| WO | 2019210079 | 10/2019 |
| WO | 2019246412 | 12/2019 |
| WO | 2020036182 | 2/2020 |
| WO | 2020160839 A1 | 8/2020 |
| WO | 2021134087 | 7/2021 |

OTHER PUBLICATIONS

Bertera, J.H., et al., "Stabilized Retinal Mapping of Known Retinal Loci," Proceedings of the Annual Northeast Bioengineering Conference, IEEE, vol. Conf. 14, No. 1988, XP000010509 (Mar. 10, 1988).

Girish et al. Segmentation of Intra-Retinal Cysts From Optical Coherence Tomography Images Using a Fully Convolutional Neural Network Model. IEEE Journal of Biomedical and Health Informatics, vol. 23, No. 1, Jan. 2019, pp. 296-304 (Year: 2019).

Haglund, Erik, et al., "Multi-wavelength VCSEL arrays using high-contrast gratings," Proc. of SPIE vol. 10113, 7 pages (2017).

Huang, et al., "Optical coherence tomograph," Science, 254(5035):1178-1181 (Nov. 22, 1991).

Huang, Huimin, et al., "UNET 3+: A Full-Scale Connected UNET for Medical Image Segmentation," 5 pages, retrieved from https://arxiv.org/ftp/arxiv/papers/2004/2004.08790.pdf on Jun. 14, 2021.

International Search Report and Written Opinion for PCT/US2021/071033, 16 pages (dated Oct. 27, 2021).

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

Khan, Zuhaib, et al., "High-brightness and high-speed vertical-cavity surface-emitting laser arrays," Optica, 7(4):267-275 (Apr. 2020).

Kolb, Jan Philip, et al., "High-resolution retinal swept source optical coherence tomography with an ultra-wideband Fourier-domain mode-locked laser at MHz A-scan rates," Biomedical Optics Express, 9(1):120-130 (2018).

Mishra, Z., et al., "Automated Retinal Layer Segmentation Using Graph-based Algorithm Incorporating Deep-learning-derived Information," Sci Rep. 10(1):9541 (2020).

Moon, S., et al., "VCSEL-based swept source for low-cost optical coherence tomography", Biomedical Optics Express, 8(2):1110-1121 (Feb. 1, 2017).

Orr. Notal Vision—Home-Based Optical Coherence Tomograph (OCT). Slide deck (11 pgs.) (Nov. 9, 2017).

Pierro, L., et al., "Macular Thickness Interoperator and Introoperator Reproducibility in Healthy Eyes Using 7 Optical Coherence Tomography Instruments," American Journal of Ophthalmology, 150(2): 199-204, XP027174249 (Aug. 1, 2010).

Sanghoon, Kim, et al., "Design and implementation of a low-cost, portable OCT system," 9(3):1232-1243 (Mar. 1, 2018).

WO 2020/036182 A1 machine translation from Japanese to English (132 pages).

Zara, J.M., et al., "Electrostatic micromachine scanning mirror for optical coherence tomography," Optics Letters, 28(8):628-630 (Apr. 15, 2003).

\* cited by examiner

SCAN PATTERN AND SIGNAL PROCESSING FOR OPTICAL COHERENCE TOMOGRAPHY

RELATED APPLICATIONS

This application is a continuation of U.S. patent application Ser. No. 17/248,870, filed Feb. 11, 2021, now U.S. Pat. No. 11,369,266, issued Jun. 28, 2022, which is a continuation of U.S. patent application Ser. No. 16/947,728, filed Aug. 13, 2020, now U.S. Pat. No. 10,959,613, issued Mar. 30, 2021, which claims the benefit under 35 U.S.C. § 119(e) of U.S. Provisional Patent Application No. 62/706,193, filed Aug. 4, 2020, the entire disclosures of which are incorporated herein by reference.

The subject matter of the present application is related to U.S. Provisional Patent Application No. 62/953,827, filed Dec. 26, 2019, the entire disclosure of which is incorporated herein by reference.

BACKGROUND

The eye is critical for vision, and people need to see. The eye has a cornea and lens that refract light and form an image on the retina. The retina generates electrical signals in response to the image formed thereon, and these electrical signals are transmitted to the brain via the optic nerve. The fovea and macula of the retina have an increased density of cones in relation to other areas of the retina and provide crisp, sharp vision. Unfortunately, diseases of the retina can adversely affect vision even though other parts of the eye, such as the cornea and lens are healthy.

Retinal thickness can be used to diagnose and monitor the health of the retina. Many patients who have been diagnosed with retinal vascular diseases and other diseases or conditions have an elevated retinal thickness and take or are treated with medications. Macular edema is an example of elevated retinal thickness which is often related to other diseases such as diabetes. Macular edema can also be related to other diseases such as age-related macular degeneration, uveitis, blockage of retinal vasculature, and glaucoma, for example. It would be helpful to know quickly if a medication is not working or requires re-administration so that treatment can be modified accordingly, and vision preserved. One way to do this is by making regular measurements of the thickness of a patient's retina. One technique used to measure the thickness of the retina is optical coherence tomography (OCT).

Unfortunately, many prior OCT systems are overly complex and expensive and not well-suited to monitoring retinal thickness regularly, such as on a weekly or daily basis. The prior standard of eye care involves a visit to a health care provider who measures retinal thickness, but such visits require scheduling and appointments and can become expensive, especially if conducted on a weekly or daily basis. Many of the prior OCT systems are not well-suited for in-home monitoring or mobile health care. Such prior systems typically weigh more than a person can easily carry and are not-well suited to travel with the patient. In addition, the prior OCT systems are more complex than would be ideal, and not well-suited for everyday use and hazards such as being dropped. The prior cost of an OCT system may exceed what a typical patient can afford. Furthermore, use of a prior OCT system may require a trained operator. For the above reasons, in-home monitoring of retinal thickness has not been adopted as the prior standard of care and care of patients with retinal disease can be less than ideal in many instances.

In light of the above, it would be helpful to have improved OCT systems and methods to measure thickness of the retina. Ideally, such systems would be compact, handheld, provide in-home monitoring, allow the patient to measure himself or herself, and be robust enough to be handled by a patient. Further, it is desirable for an in-home OCT system to capable of generating images and data that can be used by a physician to assist in diagnosing various diseases of the eye or other conditions based on changing the operation of the OCT and the data collected by the device. This would increase the utility and value of an in-home OCT system.

SUMMARY

The optical coherence tomography (OCT) system and methods disclosed herein allow in-home and mobile monitoring of retinal thickness. Although specific reference is made to measuring retinal thickness, the OCT system and methods disclosed herein will find application in many fields, such as microscopy, metrology, aerospace, astronomy, telecommunications, medicine, pharmaceuticals, dermatology, dentistry, and cardiology.

In some embodiments, the OCT system may be operated with a specific scanning pattern for the measurement beam to enable the collection of data and provide more precise measurement of certain areas of the eye. The scanning pattern may result from moving a mirror that is part of the OCT system in response to a driving signal. The mirror intercepts a measurement beam generated by a light source and directs the beam to follow a trajectory that varies with the motion of the mirror, forming a predefined scan pattern. In some embodiments, data collected from using a scan pattern may be interpolated, extrapolated, or otherwise processed to obtain data that would be obtained from using a different scan pattern. This may assist a physician to better understand conditions in different regions of the eye or to compare scans taken with different scan patterns as part of monitoring the health of a patient's eyes.

In some embodiments, the OCT system comprises an interferometer, a position sensor, a three-axis translation stage, and a processor configured with instructions to scan the eye using a specific scan pattern, where that scan pattern comprises a continuous trajectory and includes a plurality of lobes. A measurement beam generated by a light source may be turned on to generate measurement data during certain sections of the trajectory and turned off during other sections of the trajectory. Thus, as the measurement beam traces over the desired scan pattern trajectory, measurement data is collected at some points along the trajectory and is not collected at other points. In some embodiments, measurement data may be collected at a greater number of points along a first section of the trajectory and at fewer (or no) points along a second section of the trajectory. In some embodiments, the instructions may cause the OCT system to move at least a portion of the interferometer into alignment with the eye in response to a measured position of the eye, which can facilitate alignment of the eye. In some embodiments, the OCT system comprises a fixation target coupled to a lens for the patient to view the fixation target through the lens, in which the lens comprises an optical element of the OCT interferometer and also transmits an OCT measurement beam. In some embodiments, the processor is configured with instructions to change a distance between the lens and the fixation target in order to compensate for a refractive error of the eye. In some embodiments, the processor is configured with instructions to move the three-axis translation stage to align the lens laterally with the eye in response to a lateral position of the eye measured with the position sensor, and to position the lens at a target vertex distance from the cornea in response to the position sensor.

In some embodiments, the processor is configured with instructions to move the fixation target and the lens with the three-axis translation stage and to move the lens relative to the fixation target to change the relative fixation to obtain measurements on different retinal locations, to compensate for the refractive error and maintain the vertex distance between the lens and the cornea. In some embodiments, the fixation target is moved toward the eye to correct for myopia while the vertex distance is maintained by moving the lens toward the fixation target. In some embodiments, the three-axis translation stage is moved with three actuators, and the lens is moved with a fourth actuator to maintain the vertex distance.

In some embodiments, the processor is configured with instructions to translate the fixation target and the lens to a plurality of positions corresponding to a plurality of refractive errors, and to measure the luminous intensity of the beam reflected from the eye at each of the plurality of locations. The processor can determine a distance between the lens and fixation target that corresponds to correction of the refractive error, in response to the luminous intensity at each of the plurality of locations. In some embodiments, the luminous intensity comprises a peak luminous intensity of the OCT beam measured at the detector without interference between a measurement arm and the reference arm. In some embodiments, the optical path difference (OPD) between a measurement arm and a reference arm of the OCT interferometer is adjusted with a fifth actuator. Alternatively, the OCT measurement beam may comprise a sufficient coherence length and sampling frequency to perform the OCT measurement without adjusting the OPD when the lens and fixation target have been positioned for the OCT measurement with appropriate movement of the translation stage and the lens.

In some embodiments, an OCT system to measure a retina of an eye comprises an interferometer with an OCT measurement beam, a visual fixation target configured to move to a plurality of positions relative to the beam, and a position sensor to measure a position of the eye. A processor is operatively coupled to the interferometer, the fixation target and the position sensor, in which the processor is configured with instructions to move the fixation target to the plurality of positions and measure the position of the eye and the retinal data at each of the plurality of positions.

In some embodiments, an OCT system for use in measuring a retina as part of an eye health monitoring and diagnosis system comprises an OCT interferometer, where the interferometer comprises a light source or measurement beam and a scanner for moving the beam on the retina of a patient's eye, and a processor configured to execute instructions to cause the scanner to move the measurement beam on the retina in a scan pattern. The measurement beam may be caused to move on the retina by the motion of a mirror that intercepts and redirects the measurement beam. The mirror position may be altered by the application of a drive signal to one or more actuators that respond to the drive signal by rotating the mirror about an axis or axes.

In some embodiments, the processor may execute instructions to access measurement data detected by a detector that is part of the OCT interferometer. In some embodiments, the processor may execute instructions to process the accessed data to generate measurement data that would result from a different scan pattern. This may assist in obtaining more precise measurements of the thickness of the retina and using those measurements in evaluating the health of a patient's eyes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
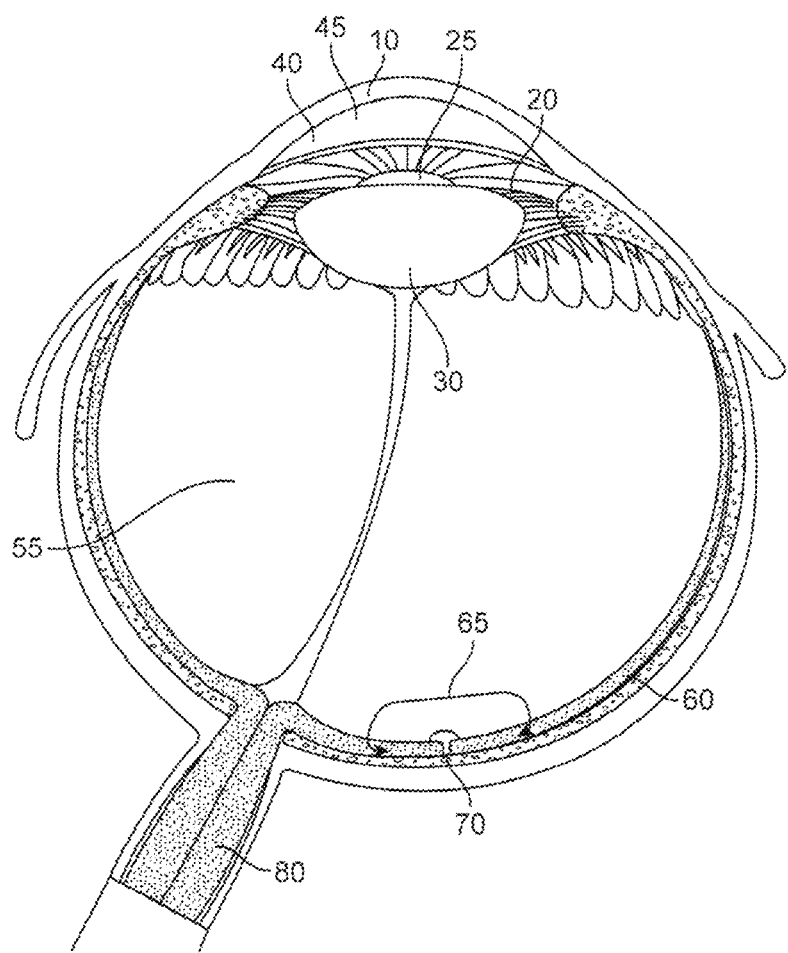
FIG. 1A shows a simplified diagram of the human eye.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed. For example, although reference is made to measuring a thickness of a sample such as the retina, the methods and apparatus disclosed herein can be used to measure many types of samples, such as other tissues of the body and non-tissue material. While reference is made to generating maps of retinal thickness, the methods and apparatus disclosed herein can be used to generate images of retinal samples, such as cross sectional or tomographic images.

The presently disclosed systems and methods are well suited for incorporation with prior OCT approaches. The OCT interferometer may comprise one or more of a time domain OCT interferometer, a swept source OCT interferometer, spectral domain OCT interferometer or a multiple reflectance OCT interferometer. Although reference is made to a swept source VCSEL with a limited range of sweeping and the use of a plurality of VCSELs, the light source may comprise any suitable light source such as a MEMS tunable VCSEL capable of sweeping over a range of wavelengths from about 20 nm to about 100 nm or more. Although reference is made to retinal thickness maps, in some embodiments, the OCT measurement systems and apparatus are configured to generate 3D tomographic images of the retina. In some embodiments, the 3D tomographic images of the retina comprise high resolution image of the retina, with a spatial resolution along the OCT measurement beam within a range from 4 to 25 microns, for example with resolution within a range from 2 to 10 microns.

The presently disclosed systems and methods can be configured in many ways. In some embodiments, the OCT system comprises a binocular device, in which one eye is measured and the other eye is presented with a stimulus such as a fixation stimulus. Alternatively, the OCT system may comprise a monocular device, in which one eye is measured at a time and only the measured eye is presented with a fixation stimulus, although the fellow eye may be covered with an occluder, for example.

The compact OCT system disclosed herein is well-suited for use with many prior clinical tests, such as retinal thickness measurements. In some cases, the OCT system is used by the patient, or by a health care provider. In many instances the patient can align himself with the system, although another user can align the patient with the system and take the measurement. In some embodiments, the OCT system is integrated with prior software and systems to provide additional information to healthcare providers and can provide alerts in response to changes in retinal thickness. The alerts are optionally sent to the patient, caregiver, and health care providers when corrective action should be taken such as a change in medication, dosage, or a reminder to take medication.

As used herein, the term "retinal thickness (RT)" refers to a thickness of the retina between layers used to evaluate the thickness of a retina of a patient. The RT may correspond to a thickness of the retina between an anterior surface of the retina and external limiting membrane, for example.

As used herein, the term "retinal layer thickness (RLT)" refers to the thickness of one or more optically detectable layers of the retina. The optically detectable layers of the retina may comprise a thickness of the retina extending between the external limiting membrane and the retinal pigment epithelium (RPE), for example.

FIG. 1A shows a simplified diagram of the human eye. Light enters the eye through the cornea 10. The iris 20 controls the amount of light allowed to pass by varying the size of the pupil 25 that allows light to proceed to the lens 30. The anterior chamber 40 contains aqueous humor 45 which determines the intraocular pressure (TOP). The lens 30 focuses light for imaging. The focal properties of the lens are controlled by muscles which reshape the lens. Focused light passes through the vitreous chamber, which is filled with vitreous humor 55. The vitreous humor maintains the overall shape and structure of the eye. Light then falls upon the retina 60, which has photosensitive regions. In particular, the macula 65 is the area of the retina responsible for receiving light in the center of the visual plane. Within the macula, the fovea 70 is the area of the retina most sensitive to light. Light falling on the retina generates electrical signals which are passed to the optic nerve 80 and then to the brain for processing.

Several disorders give rise to reduced optical performance of the eye. In some cases, the intraocular pressure (TOP) is either too high or too low. This is caused, for instance, by too high or too low of a production rate of aqueous humor in the anterior chamber or drainage of aqueous humor from the anterior chamber, for example. In other cases, the retina is too thin or too thick. This arises, for instance, due to the buildup of fluid in the retina. Diseases related to an abnormal retinal thickness (RT) include glaucoma, macular degeneration, diabetic retinopathy, macular edema and diabetic macular edema, for example. In some cases, a healthy range of RT is from 175 μm thick to 225 μm thick. In general, abnormalities in either the IOP or the RT or both are indicative of the possible presence of one of several ophthalmological diseases. Additionally, the IOP or the RT vary in response to ophthalmological treatments or other procedures. Therefore, it is desirable to have a means to measure the IOP and/or RT for diagnosis of ophthalmological diseases and to assess the effectiveness of treatments for a given patient. In some cases, it is desirable to measure the thickness of one or more retinal layers, for example the thickness of a plurality of layers. In addition, it is desirable to process data obtained from an OCT system to assist in identifying fluid pockets or regions in the eye, as these may indicate a change in eye health.

The systems and methods disclosed herein relate to the use of optical coherence tomography (OCT) to measure the RT or RLT at multiple points in time. For instance, a patient measures their RT or RLT at multiple time points to track the progression of an ophthalmological disease such as glaucoma or macular edema over time. As another example, a patient measures their RT or RLT at multiple time points to track their response to a pharmaceutical or other treatment. In some cases, the system produces an alert when one or more recent measurements of the RT or RLT deviate significantly from previous measurements. In some cases, the system alerts the patient or the patient's physician of the change. In some instances, this information is be used to schedule a follow-up appointment between the patient and physician to, for instance, attempt a treatment of an ophthalmological illness, discontinue a prescribed treatment, or conduct additional testing.

Figure 1B:
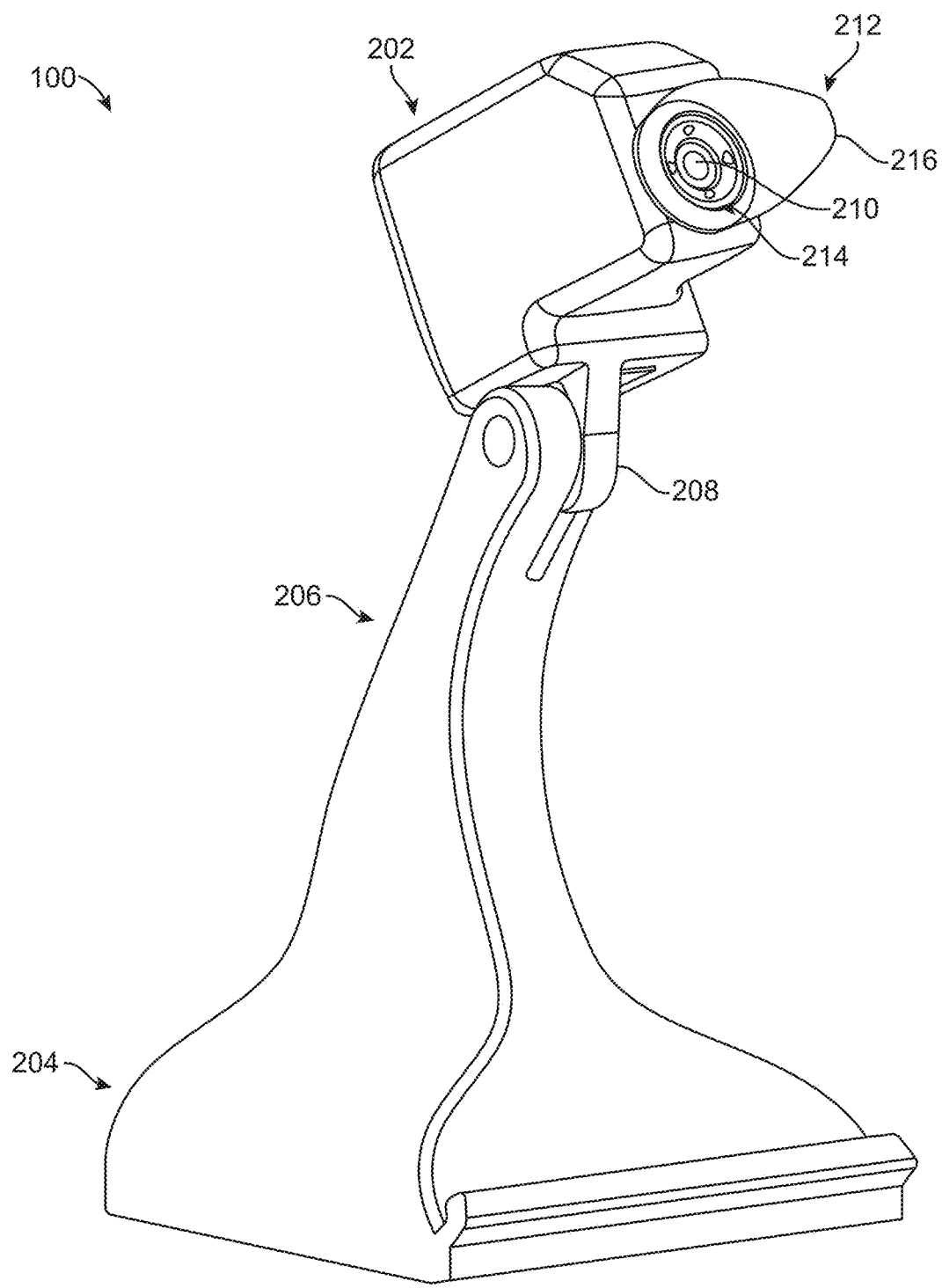
FIG. 1B shows a perspective view of a monocular optical coherence tomography (OCT) device for measuring eyes of a user, in accordance with some embodiments.

FIG. 1B shows a perspective view of a monocular optical coherence tomography (OCT) device 100 for measuring eyes of a user, in accordance with some embodiments. The OCT device 100 includes a head 202, a base 204, and a neck 206 therebetween. The head 202 is connected to the neck 206 by a coupling 208 that allows articulation of the head 202 in some embodiments. The head may be covered with a housing that encloses optical modules, scanning modules, and other related circuitry and modules to allow the OCT device 100 to measure eyes of a user, one eye at a time.

In some embodiments, the head 202 further includes a lens 210, and eyecup 212, and one or more LED lights 214. The lens 210 may be configured to direct one or more light sources from within the head 202 to focus on the retina of an eye. The eyecup 212 may be configured to locate the head of a patient, and thereby locate an eye of a patient for scanning and testing. The eyecup 212 may be rotatable, so that a protruding portion 216 may be located adjacent to an eye of a patient and extend along the side of the head (e.g., adjacent the patient's temple) when the patient's head is properly oriented to the OCT device 100. The eyecup 212 may be coupled to a sensor configured to detect the rotational orientation of the eyecup 212. In some embodiments, the OCT device 100 is configured to detect the rotational orientation of the eyecup 212 and thereby determine whether the patient has presented her right eye or left eye for scanning and measuring. More particularly, in some embodiments, the protruding portion 216 of the eyecup 212 may extend to be adjacent to either the right temple or the left temple of a patient, and thereby determine which eye of the patient is being measured. In some embodiments, eyecup 212 comprises a patient support. The patient support may comprise a headrest or a chinrest, either alternatively or in combination with the eyecup 212.

In some embodiments, a coupling 208 connects the head 202 to the neck 206 and allows a pivotal movement about the coupling. The coupling 208 may be any suitable coupling, which may be rigid, articulating, rotational, or pivotal according to embodiments. In some instances, the coupling includes a threaded fastener and a threaded nut to tighten the head against the neck in a desired orientation. The threaded nut may be operable by hand, and may comprise a knurled knob, a wing nut, a star nut, or some other type of manually operated tightening mechanism. The coupling may alternatively or additionally comprise any suitable member that allows adjustment of the angle of the head relative to the neck, and may include a cam, a lever, a detent, and may alternatively or additionally include friction increasing structures, such as roughened surfaces, peaks and valleys, surface textures, and the like.

Figure 2:
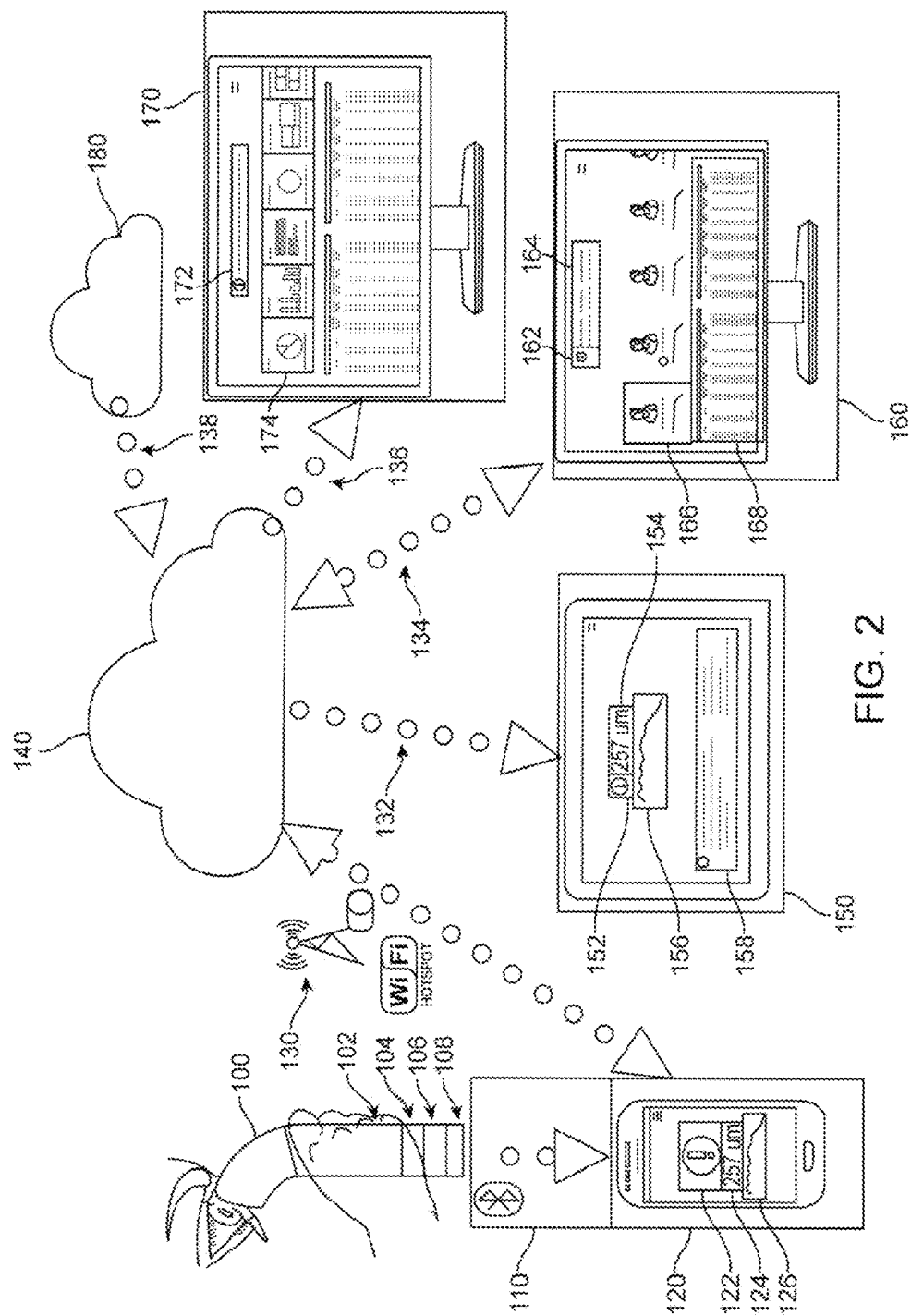
FIG. 2 shows a schematic of a system allowing a patient to measure retinal thickness (RT) at multiple time points and to communicate the results, in accordance with some embodiments.

FIG. 2 shows a schematic of a system allowing a patient to measure RT or RLT at multiple time points and to communicate the results, in accordance with some embodiments. The patient looks into a handheld OCT device 100 to obtain a measurement of the RT or RLT. In some embodiments, the handheld OCT device comprises optics 102, electronics 104 to control and communicate with the optics, a battery 106, and a transmitter 108. In some instances, the transmitter is a wired transmitter. In some cases, the transmitter is a wireless transmitter. In some cases, the handheld OCT device 100 communicates the results via a wireless communication channel 110 to a mobile patient device 120 such as the patient's smartphone or other portable electronic device. In some cases, the wireless communication is via Bluetooth communication. In some embodiments, the wireless communication is via Wi-Fi communication. In other embodiments, the wireless communication is via any other wireless communication known to one having skill in the art. Although reference is made to wireless communication, in some embodiments the OCT device connects by wired communication to the patient mobile device and the patient mobile device connects wirelessly to a remote server such as a cloud based server.

In some cases, the results are fully processed measurements of the RT. In some cases, all processing of the OCT data is performed on the handheld OCT device. For instance, in some embodiments, the handheld OCT device includes hardware or software elements that allow the OCT optical waveforms to be converted into electronic representations. In some cases, the handheld OCT device further includes hardware or software elements that allow processing of the electronic representations to extract, for instance, a measurement of the RT.

In some cases, the results are electronic representations of the raw optical waveforms obtained from the OCT measurement. For instance, in some embodiments, the handheld OCT device includes hardware or software elements that allow the OCT optical waveforms to be converted into electronic representations. In some cases, these electronic representations are then passed to the mobile patient device for further processing to extract, for instance, a measurement of the RT.

In some cases, the patient receives results and analysis of the RT or RLT measurement on the patient mobile app. In some embodiments, the results include an alert 122 alerting the patient that the results of the measurement fall outside of a normal or healthy range. In some cases, the results also include a display of the measured value 124. For instance, in some cases a measurement of the RT or RLT produces a result of 257 μm. In some instances, this result falls outside of a normal or healthy range. This causes the system to produce an alert and to display the measured value of 257 μm on the patient mobile app. In some embodiments, the alert is transmitted to a healthcare provider, such as a treating physician. In some embodiments, the results also include a chart 126 showing a history of the patient's RT or RLT over multiple points in time.

In some instances, the patient mobile device communicates the results of the measurement via a communication means 130 to a cloud-based or other network-based storage and communications system 140. In some embodiments, the communication means is a wired communication means. In some embodiments, the communication means is a wireless communication means. In some cases, the wireless communication is via Wi-Fi communication. In other cases, the wireless communication is via a cellular network. In still other cases, the wireless communication is via any other wireless communication known to one having skill in the art. In specific embodiments, the wireless communication means is configured to allow transmission to or reception from the cloud-based or other network-based storage and communications system.

Once stored in the cloud, the results are then transmitted to other devices, in specific embodiments. In some cases, the results are transmitted via a first communication channel 132 to a patient device 150 on the patient's computer, tablet, or other electronic device. In some embodiments, the results are transmitted via a second communication channel 134 to a physician device 160 on the patient's physician's computer, tablet, or other electronic device. In some instances, the results are transmitted via a third communication channel 136 to an analytics device 170 on another user's computer, tablet, or other electronic device. In some embodiments, the results are transmitted via a fourth communication channel 138 to a patient administration system or hospital administration system 180. In some cases, each of the devices has appropriate software instructions to perform the associated function(s) as described herein.

In specific embodiments, the first communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is via any other wired or wireless communication channel or method known to one having skill in the art. In some embodiments, the first communication channel is configured to allow transmission to or reception from the cloud-based or other network-based storage and communications system. In some cases, the first communication channel is configured to only allow reception from the cloud-based or other network-based storage and communications system.

In some cases, the second communication channel is a wired communication channel or a wireless communication channel. In some instances, the communication is via Ethernet. In specific embodiments, the communication is via a local area network (LAN) or wide area network (WAN). In other embodiments, the communication is via Wi-Fi. In still other embodiments, the communication is via any other wired or wireless communication channel or method known to one having skill in the art. In some cases, the second communication channel is configured to allow transmission to or reception from the cloud-based or other network-based storage and communications system. In some embodiments, the second communication channel is configured to only allow reception from the cloud-based or other network-based storage and communications system.

In specific cases, the third communication channel is a wired communication channel or a wireless communication channel. In some instances, the communication is via Ethernet. In other instances, the communication is via a local area network (LAN) or wide area network (WAN). In still other instances, the communication is via Wi-Fi. In yet other instances, the communication is via any other wired or wireless communication channel or method known to one having skill in the art. In some embodiments, the third communication channel is configured to allow transmission to or reception from the cloud-based or other network-based storage and communications system. In some cases, the third communication channel is configured to only allow reception from the cloud-based or other network-based storage and communications system.

In some embodiments, the fourth communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is any other wired or wireless communication channel or method known to one having skill in the art. In some instances, the fourth communication channel is configured to allow transmission to or reception from the cloud-based or other network-based storage and communications system. In other cases, the fourth communication channel is configured to only allow reception from the cloud-based or other network-based storage and communications system.

A determination of the RT or RLT can be performed at many locations. For instance, a determination of the RT or RLT may be performed on the handheld OCT device. In some cases, a determination of the RT or RLT is performed at a location near to the handheld OCT device, such as by a smartphone or other portable electronic device. In some embodiments, a determination of the RT or RLT is performed on the cloud-based storage and communications system. In some instances, the handheld OCT device is configured to compress measurement data and transmit the compressed measurement data to the cloud-based storage and communications system. Alternatively or in combination, other components of the OCT system, such as a mobile device operatively coupled to the OCT device, can be configured to compress the measurement data and transmit the compressed measurement data to the cloud-based storage and communication system, for example.

In some embodiments, the patient receives results and analysis of the RT or RLT measurement on the patient device 150. In some instances, the results include an alert 152 alerting the patient that the results of the measurement fall outside of a normal or healthy range. In some cases, the results also include a display of the measured value 154. For instance, in some cases, a measurement of the RT or RLT produces a result of 257 µm. This result falls outside of a normal or healthy range. In some cases, this causes the system to produce an alert and to display the measured value of 257 µm on the patient device. In specific cases, the results also include a chart 156 showing a history of the patient's RT or RLT over multiple points in time. In some cases, the patient device also displays instructions 158 for the patient to follow. In some instances, the instructions instruct the patient to visit their physician. In some embodiments, the instructions include the patient's name, date of most recent RT or RLT measurement, and next scheduled visit to their physician. In other cases, the instructions include more information. In still other cases, the instructions include less information.

In some embodiments, the patient's physician receives the results and analysis of the RT or RLT measurement on the physician device 160. In some instances, the results include an alert 162 alerting the physician that the results of the measurement fall outside of a normal or healthy range. In some cases, the results also include an alert 164 informing the physician that the patient's measurement falls outside of a normal or healthy range. In some embodiments, the alert includes a suggestion that the physician call the patient to schedule an appointment or to provide medical assistance. In some embodiments, the results also include a display 166 showing the most recent measurements and historical measurements for each of the physician's patients. For instance, in some instances, a measurement of the RT or RLT produces a result of 257 µm. This result falls outside of a normal or healthy range. In some cases, this causes the system to produce an alert and to display the measured value of 257 µm on the physician app. In specific cases, the physician device also displays contact and historical information 168 for each of the physician's patients.

In some embodiments, the other user receives results and analysis of the RT or RLT measurement on the analytics device 170. In some instances, the other user is a researcher investigating the efficacy of a new form of treatment. In other cases, the other user is an auditor monitoring the outcomes of a particular physician or care facility. To protect the patient's privacy, in some cases the analytics device is restricted to receive only a subset of a given patient's information. For instance, the subset is restricted so as not to include any personally identifying information about a given patient. In some cases, the results include an alert 172 alerting or indicating that a large number of abnormal or unhealthy measurements have been obtained in a specific period of time. In some cases, the results include one or more graphical representations 174 of the measurements across a population of patients.

In some cases, the results and analysis on the analytics device comprise disease information such as a physician-confirmed diagnosis. In some cases, the results and analysis comprise anonymized patient data such as age, gender, genetic information, information about the patient's environment, smoking history, other diseases suffered by the patient, etc. In some cases, the results and analysis comprise anonymized treatment plans for the patient, such as a list of prescribed medications, treatment history, etc. In some cases, the results and analysis comprise measurement results, such as the results of an RT or RLT measurement, a visual function test, or the patient's compliance with a course of treatment. In some cases, the results and analysis comprise data from an electronic medical record. In some cases, the results and analysis comprise diagnostic information from visits to a patient's medical provider, such as the results of an OCT scan acquired by the patient's medical provider.

In some embodiments, the patient's clinical, hospital, or other health provider receives results and analysis of the RT or RLT measurement on the patient administration system or hospital administration system 180. In some cases, this system contains the patient's electronic medical record. In some cases, the results and analysis provide the patient's health provider with data allowing the provider to update the treatment plan for the patient. In some instances, the results and analysis allow the provider to decide to call the patient in for an early office visit. In some instances, the results and analysis allow the provider to decide to postpone an office visit.

In some embodiments, one or more of the patient device, physician device, and analytics device includes a software application comprising instructions to perform the functions of the patient device, physician device, or analytics device, respectively, as described herein.

Figure 3A:
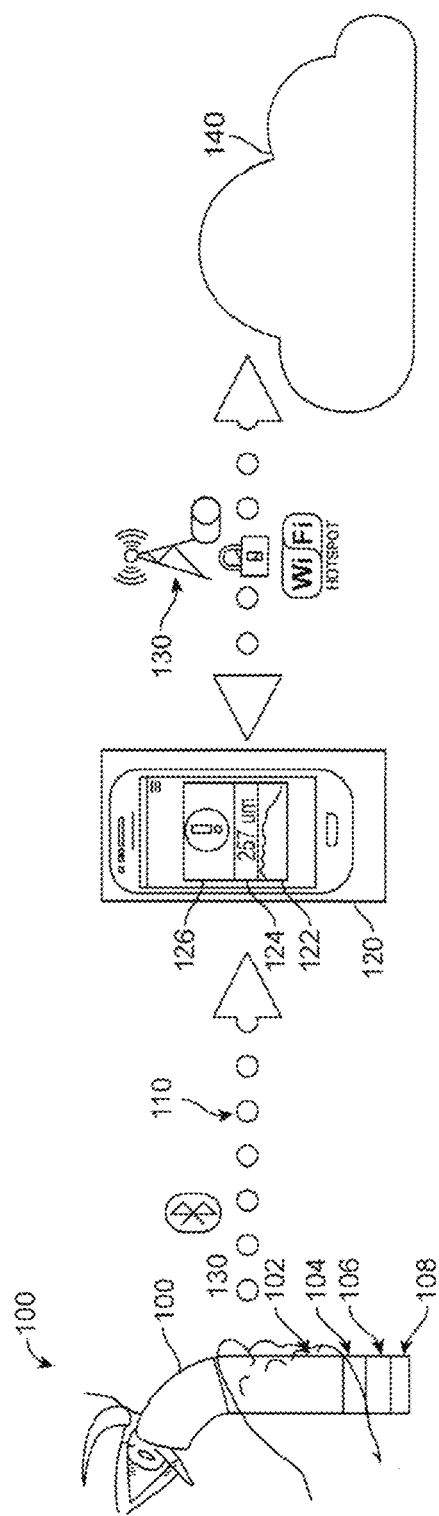
FIG. 3A shows a handheld optical coherence tomography device utilizing Bluetooth communication, in accordance with some embodiments.

FIG. 3A shows a handheld OCT device utilizing short-range wireless communication, in accordance with some embodiments. In some embodiments, the handheld OCT device 100 comprises optics 102, electronics to control and communicate with the optics 104, a battery 106, and a wireless transmitter 108. In some cases, the wireless transmitter is a Bluetooth transmitter. In some instances, the results from one or more RT or RLT measurements are stored on the handheld OCT device until an authorized user, such as the patient or another person designated by the patient, opens the patient mobile device on a smartphone or other portable electronic device. Once opened, the patient mobile device application establishes wireless communication with the handheld OCT device. In some cases, the communication is via a Bluetooth wireless communication channel 110. In some instances, the handheld OCT device communicates the results via the Bluetooth channel to a mobile patient device 120 on the patient's smartphone or other portable electronic device.

In some instances, the results include an alert 122 alerting the patient that the results of the measurement fall outside of a normal or healthy range. In specific embodiments, the results also include a display of the measured value 124. For instance, a measurement of the RT or RLT produces a result of 257 µm in some cases. This result falls outside of a normal or healthy range. In some cases, this causes the system to produce an alert and to display the measured value of 257 µm on the patient mobile app. In specific embodiments, the results also include a chart 126 showing a history of the patient's RT or RLT over multiple points in time.

In some cases, the patient mobile device application communicates the results of the measurement via a wireless communication means 130 to a cloud-based or other network-based storage and communications system 140. In some instances, the wireless communication is via Wi-Fi communication. In other cases, the Wi-Fi communication is via a secure Wi-Fi channel. In still other cases, the wireless communication is via a cellular network. In specific embodiments, the cellular network is a secure cellular network. In other embodiments, the transmitted information is encrypted. In some cases, the communication channel is configured to allow transmission to or reception from the cloud-based or other network-based storage and communications system. In some cases, data is stored on the smartphone or other portable electronic device until the smartphone or other portable electronic device connects to a Wi-Fi or cellular network.

In some cases, the patient mobile device application has a feature which notifies the patient, or another person designated by the patient, when too much time has elapsed since the patient mobile device application was last opened. For instance, in some cases this notification occurs because the patient has not acquired measurements of the RT or RLT as recently as required by a measuring schedule set by their physician or other healthcare provider. In other cases, the notification occurs because the handheld OCT device has been storing the results of too many measurements and needs to transmit the data to the patient's smartphone. In specific embodiments, the patient mobile device application communicates with the cloud-based or other network-based storage and communications system to display a complete set of patient data.

Figure 3B:
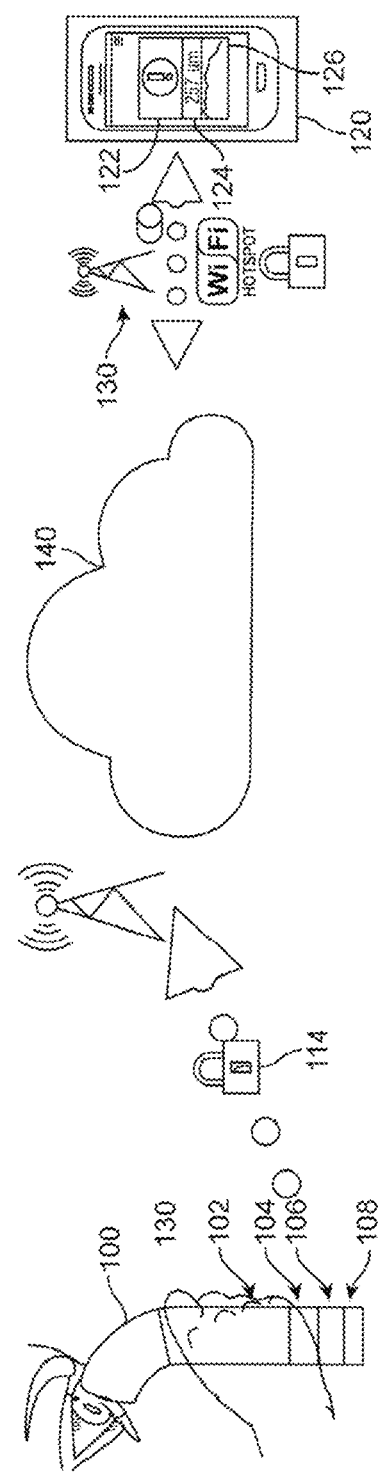
FIG. 3B shows a handheld OCT device utilizing the Global System for Mobile Communications (GSM), in accordance with some embodiments.

FIG. 3B shows a handheld OCT device capable of communicating directly with a cloud-based storage and communication system without reliance on a user device such as a smartphone, in accordance with some embodiments. In some embodiments, the handheld OCT device 100 comprises optics 102, electronics to control and communicate with the optics 104, a battery 106, and a wireless transmitter 108. In some cases, the wireless transmitter is a GSM transmitter. In some instances, the results from one or more RT or RLT measurements are stored on the handheld OCT device. In some cases, the GSM transmitter establishes wireless communication with a cloud-based or other network-based storage and communications system 140 via a wireless communication channel 114. In specific cases, the wireless communication is via a GSM wireless communication channel. In other embodiments, the system utilizes third generation (3G) or fourth generation (4G) mobile communications standards. In such cases, the wireless communication is via a 3G or 4G communication channel.

In specific embodiments, the patient mobile device 120 receives the results of the measurement via a wireless communication means 130 from the cloud-based or other network-based storage and communications system 140. In some cases, the wireless communication is via Wi-Fi communication. In some cases, the Wi-Fi communication is via a secure Wi-Fi channel. In other cases, the wireless communication is via a cellular network. In some cases, the cellular network is a secure cellular network. In specific instances, the transmitted information is encrypted. In some embodiments, the communication channel is configured to allow transmission to or reception from the cloud-based or other network-based storage and communications system.

Once obtained from the cloud-based or other network-based storage and communications system, the results of the RT or RLT measurement are viewed in the patient mobile application, in some instances. In some cases, the results include an alert 122 alerting the patient that the results of the measurement fall outside of a normal or healthy range. In some instances, the results also include a display of the measured value 124. For instance, in some cases a measurement of the RT or RLT produces a result of 257 µm. This result falls outside of a normal or healthy range. In specific embodiments, this causes the system to produce an alert and to display the measured value of 257 µm on the patient mobile application. In some embodiments, the results also include a chart 126 showing a history of the patient's RT or RLT over multiple points in time.

In some cases, the patient mobile device application has a feature which notifies the patient, or another person designated by the patient, when too much time has elapsed since the patient mobile device application was last opened. For instance, in some cases this notification occurs because the patient has not acquired measurements of the RT or RLT as recently as required by measuring schedule set by their physician or other healthcare provider. In other cases, the notification occurs because the handheld OCT device has been storing the results of too many measurements and needs to transmit the data to the patient's smartphone. In specific embodiments, the patient mobile device communicates with the cloud-based or other network-based storage and communications system to display a complete set of patient data.

In some cases, the handheld OCT device comprises both a short-range transmitter and a GSM, 3G, or 4G transmitter. In some instances, the short-range transmitter is a Bluetooth transmitter. In some cases, the handheld OCT device communicates directly with the patient mobile device application on a smartphone or other portable electronic device through the Bluetooth wireless communication channel. In some embodiments, the handheld OCT also communicates with the cloud-based or other network-based storage and communications system through the GSM, 3G, or 4G wireless communication channel. In specific cases, the cloud-based system then communicates with the patient mobile device application through a Wi-Fi, cellular, or other wireless communication channel. Alternatively, the Bluetooth transmitter is built into a docking station. In some instances, this allows for the use of older devices for patients who lack a smartphone. In some cases, the docking station also includes a means for charging the battery of the handheld OCT device.

In some cases, the handheld OCT device of FIGS. 3A and 3B is configured to be held in close proximity to the eye. For instance, in specific embodiments, the device is configured to be held in front of the eye with the detector at a distance of no more than 200 mm from the eye. In other embodiments, the devices are configured to be held in front of the eye with the detector at a distance of no more than 150 mm, no more than 100 mm, or no more than 50 mm from the eye. In specific instances, the handheld OCT devices further comprise housing to support the light source, optical elements, detector, and circuitry. In some cases, the housing is configured to be held in a hand of a user. In some cases, the user holds the devices in front of the eye to direct the light beam into the eye. In some instances, the devices include a sensor to measure which eye is being measured. For instance, in specific embodiments, the devices include an accelerometer or gyroscope to determine which eye is measured in response to an orientation of the housing. The devices optionally include an occlusion structure coupled to the housing and the sensor that determines which eye is measured. The occlusion structure occludes one eye while the other eye is measured. In some cases, the devices include a viewing target to align the light beams with a portion of the retina. For instance, in specific embodiments, the devices include a viewing target to align the light beams with a fovea of the eye. In some cases, the viewing target is a light beam. In some cases, the viewing target is a light emitting diode. In other cases, the viewing target is a vertical cavity surface emitting laser (VCSEL). In still further cases, the viewing target is any viewing target known to one having skill in the art.

The optical components described herein are capable of being miniaturized so as to provide the handheld OCT device with a reduced physical size and mass, as described herein, as will be appreciated by one of ordinary skill in the art.

In some embodiments, the handheld OCT devices of FIGS. 3A and 3B are small enough and light enough to be easily manipulated with one hand by a user. For instance, in some embodiments, the device has a mass within a range from about 100 grams to about 500 grams, although the device may be heavier and may comprise a mass within a range from about 500 grams to about 1000 grams, for example. In some embodiments, the device has a mass within a range from about 200 grams to about 400 grams. In some embodiments, the device has a mass within a range from about 250 grams to about 350 grams. In specific embodiments, the device has a maximum distance across within a range from about 80 mm to about 160 mm. In specific embodiments, the device has a maximum distance across within a range from about 100 mm to about 140 mm. In specific embodiments, the device has a width within a range from about 110 mm to about 130 mm. In some embodiments, the maximum distance across comprises a length. In some embodiments, the device has a width less than its length. In specific embodiments, the device has a width within a range from about 40 mm to about 80 mm. In specific embodiments, the device has a width within a range from about 50 mm to about 70 mm. In specific embodiments, the device has a width within a range from about 55 mm to about 65 mm.

Figure 4:
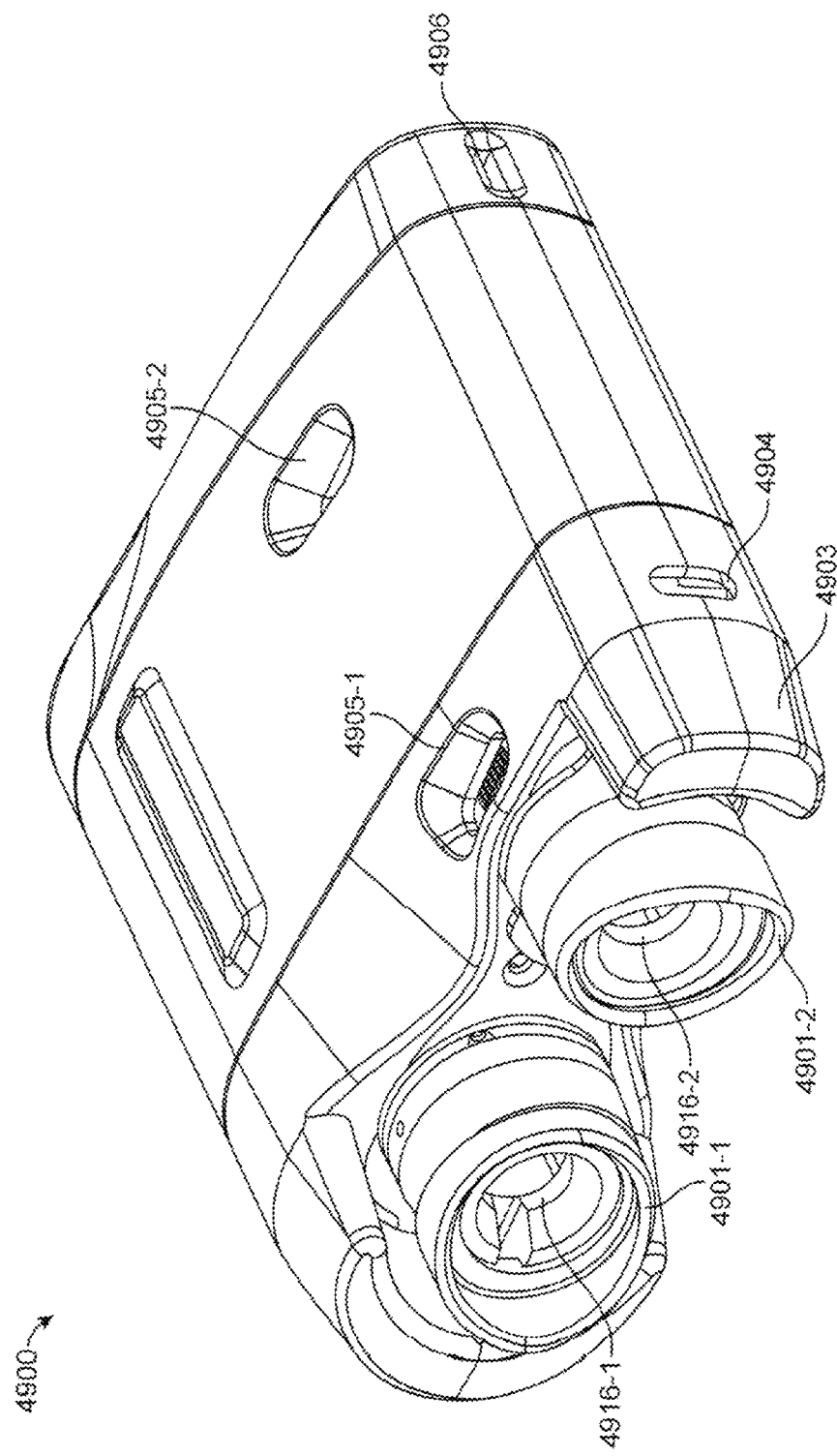
FIG. 4 shows a perspective view of a binocular OCT device for measuring eyes of a user, in accordance with some embodiments.

FIG. 4 shows a perspective view of a binocular OCT device 4900 for measuring eyes of a user, in accordance with some embodiments. The binocular OCT device 4900 comprises a first adjustable lens 4916-1 that is optically coupled to an OCT measurement system and a first fixation target configured within a handheld unit body 4903 (e.g., a housing), both of which are hidden from view in this figure. Similarly, a second adjustable lens 4916-2 may be optically coupled to the OCT measurement system and a second fixation target (hidden). The first adjustable lens 4916-1 may be part of a first free space optics that is configured to provide a fixation target and measure a retinal thickness of the user's eye, whereas the second adjustable lens 4916-2 may be part of a second free space optics that is configured to only provide a fixation target so as to reduce a number of components in the binoculars OCT device 4900. For instance, while both free space optics provide the user with a fixation target, only one of the free space optics is used to measure the retinal thickness as the binocular OCT device 4900 may be turned upside down, i.e. inverted, after the user measures a first eye such that the user may measure the other eye.

The binocular OCT device 4900, in this embodiment, comprises an interpupillary distance (IPD) adjustment mechanism 4905 that is accessible on the exterior of the handheld unit body 4903. In this embodiment, the IPD adjustment mechanism 4905 comprises two components, a first component 4905-1 that adjusts the distance between the lenses 4916-1 and 4916-2 to match the IPD of a user's pupils when the user places the binocular OCT device 4900 front of the user's eyes when the eye cups 4901-1 and 4901-2 rest on the user's face.

This IPD can be set by a healthcare professional and locked into position for the user to measure retinal thickness at home. Alternatively, the IPD can be user adjustable. A switch 4904 may be used to adjust the lenses 4916-1 and 4916-2 to match a user's refraction, i.e. eyeglass prescription. Alternatively, a mobile device, such as a tablet can be used program the refraction of each eye of the patient. For example, the user may fixate on the first fixation target with one eye and a second fixation target with another eye, and the movable lenses adjusted to the user's refraction. The switch 4904 may selectively adjust the assemblies of the lenses 4916-1 and 4916-2 within the handheld unit body 4903 to change the positioning of the lenses 4916-1 and 4916-2. These positions can be input into the device by a health care professional and stored in a processor along with an orientation from an orientation sensor as described herein. The device can be inverted, and the process repeated. Alternatively, or additionally, the prescription for each eye can be stored in the processor and the lenses adjusted to the appropriate refraction for each eye in response to the orientation of the orientation sensor.

Both of the components 4905-1 and 4905-5 may be implemented as one or more wheels that the health care professional manually rotates. Alternatively, the IPD adjustment mechanism 4905 may be motorized. In this regard, the components 4905-1 and 4905-5 may be configured as directional switches that actuate motors within the handheld unit body 4903 to rotate gears within the handheld unit body 4903 based on the direction in which the user directs the switch.

The switch 4904 can be used to adjust the focusing of the binocular OCT device 4900. For example, because the focal change effected by adjustment of the lenses 4916-1 and 4916-2 can be measured in a customary unit of refractive power (e.g., the Diopter) by adjustment of the lenses 4916-1 and 4916-2. The Diopter switch 4906 may also comprise a directional switch that actuates a motor within the handheld unit body 4903 to rotate gears within the handheld unit body 4903 based on the direction in which the healthcare professional directs the switch to adjust the refractive power of the binocular OCT device 4900. As the binocular OCT device 4900 may comprise an electronic device, the binocular OCT device 4900 may comprise a power switch 4906 to control powering of the binocular OCT device 4900.

Each of the eyecups 4901-1 and 4901-2 can be threadedly mounted and coupled to the housing to allow adjustment of the position of the eye during measurements. Work in relation to the present disclosure suggests that the eyecups can be adjusted by a healthcare professional and locked in place to allow sufficiently reproducible positioning of the eye for retinal thickness measurements as described herein. Alternatively, or in combination, an eye position sensor, such as a Purkinje image sensor can be used to determine a distance from the eye to the OCT measurement system.

The binocular OCT device 4900 may comprise appropriate dimensions and weight for in home measurements and for the user to take the binocular OCT system on trips. For example, the binocular OCT system may comprise a suitable length, a suitable width and a suitable height. The length can extend along an axis corresponding to the users viewing direction. The length can be within a range from about 90 mm to about 150 mm, for example about 130 mm. The width can extend laterally to the length and can be within a range from about 90 mm to about 150 mm for example about 130 mm. The height can be within a range from about 20 mm to about 50 mm, for example. In some embodiments, the length is within a range from about 110 mm to 210 mm, the width within a range from about 100 mm to about 200 mm and a height within a range from about 50 mm to about 110 mm. In some embodiments, a maximum distance across the device is within a range from about 200 mm to about 350 mm, for example approximately 300 mm.

The weight of the binocular OCT system can be within a range from about 1 pound to two pounds, e.g. 0.5 kg to about 1 kg.

The binocular OCT device 4900 can be configured to be dropped and still function properly. For example, the binocular OCT device can be configured to be dropped from a height of about 30 cm and still function so as to perform retinal thickness measurements accurately, e.g. with a change in measured retinal thickness of no more than the repeatability of the measurements. The binocular OCT system can be configured to be dropped from a height of about 1 meter without presenting a safety hazard, for example from glass breaking.

Figure 5:
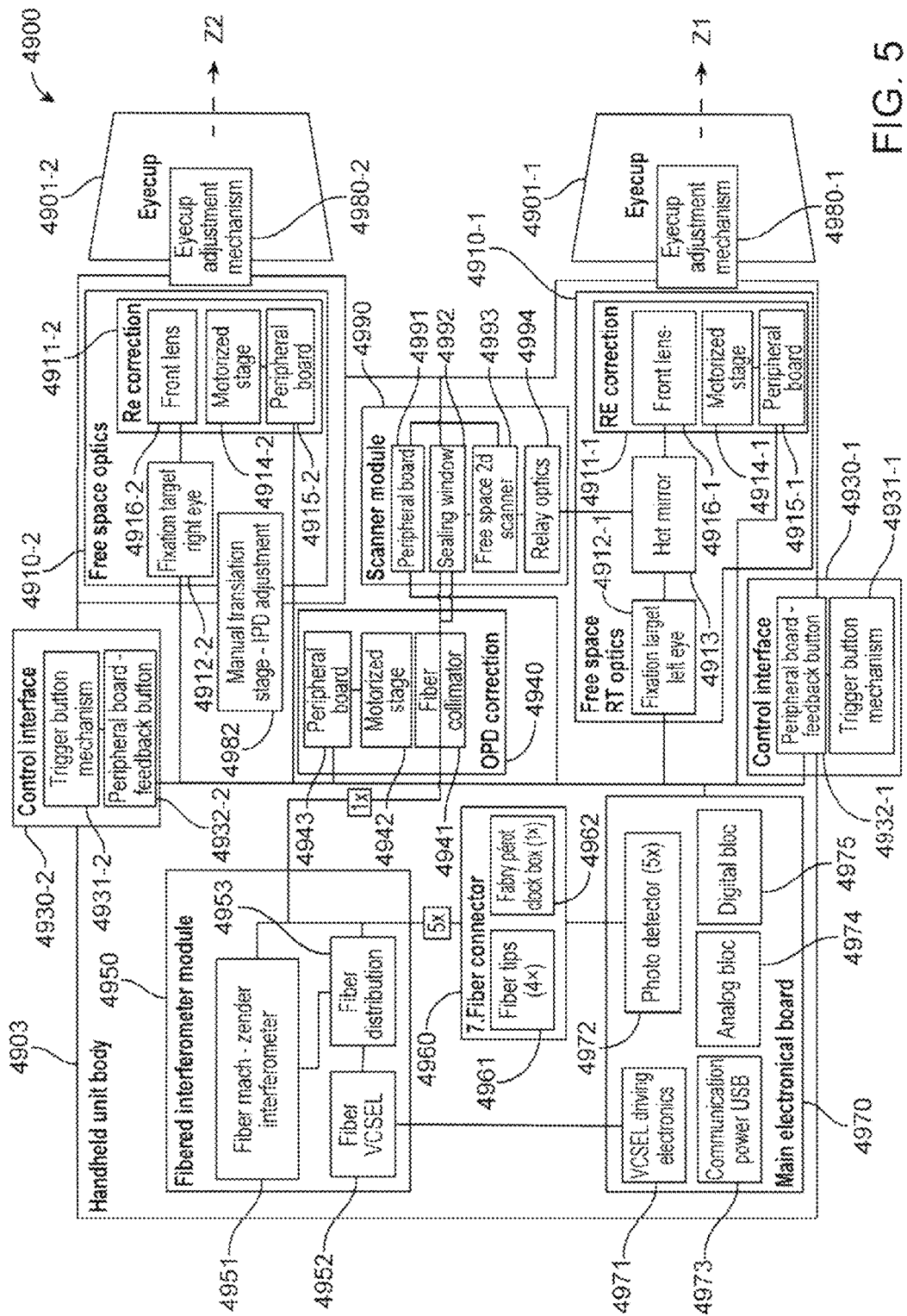
FIG. 5 shows a block diagram of the binocular OCT device illustrating various components within the handheld unit body, in accordance with some embodiments.

FIG. 5 shows a block diagram of the binocular OCT device 4900 illustrating various components within the handheld unit body 4903, in accordance with some embodiments. For instance, the binocular OCT device 4900 comprises free space optics 4910-1 and 4910-2. Each of the free space optics 4910-1 and 4910-2 comprises a fixation target 4912 for its respective eye that allows the user to fixate/gaze on the target while the user's retinal thickness is being measured, and to allow fixation with the other eye, so as to provide binocular fixation. The fixation target may comprise an aperture back illuminated with a light source such as an LED, (e.g., a circular aperture to form a disc shaped illumination target, although a cross or other suitable fixation stimulus may be used. The free space optics 4910-1 and 4910-2 may also comprise refractive error (RE) correction modules 4911-1 and 4911-2, respectively, that comprises the lenses 4916-1 and 4916-2, respectively. These lenses can be moved to preprogrammed positions corresponding to the refractive error of the appropriate eye. A peripheral board 4915-1 and 4915-2 in the free space optics modules 4910-1 and 4910-2 provides electronic control over a motorized stage 4914-1 and 4914-2, respectively to correct for the refractive error of the respective eye viewing the fixation target of the binocular OCT device 4900.

As discussed herein, the binocular OCT device 4900 may comprise eye cups 4901-1 and 4901-2 that may be used to comfortably rest the binocular OCT device 4900 on the user's face. They may also be configured to block out external light as the user gazes into the binocular OCT device 4900. The eye cups 4901 may also comprise eye cup adjustment mechanisms 4980-1 and 4980-2 that allow the health care professional and optionally the user to move the eye cups 4901-1 and 4901-2 back and forth with respect to the handheld unit body 4903 to comfortably position the eye cups on the user's face and appropriately position each eye for measurement.

In some embodiments, the binocular OCT device 4900 comprises a fibered interferometer module 4950 that comprises a single VCSEL or a plurality of VCSELs 4952. The one or more VCSELs 4952 are optically coupled to a fiber distribution module 4953, which is optically coupled to fiber Mach-Zender interferometer 4951. With embodiments comprising a plurality of VCSELs 4952, the VCSELS may each comprise a range of wavelengths different from other VCSEL 4952 in the plurality in order to extend a spectral range of light. For example, each VCSEL 4952 may pulse laser light that is swept over a range of wavelengths for some duration of time. The swept range of each VCSEL 4952 may partially overlap an adjacent swept range of another VCSEL 4952 in the plurality as described herein. Thus, the overall swept range of wavelengths of the plurality of VCSELs 4952 may be extended to a larger wavelength sweep range. Additionally, the firing of the laser light from the plurality of VCSELs 4952 may be sequential. For example, a first VCSEL of the plurality of VCSELs 4952 may sweep a laser pulse over a first wavelength for some duration. Then, a second VCSEL of the plurality of VCSELs 4952 may sweep a laser pulse over a second wavelength for some similar duration, then a third, and so on.

The laser light from the VCSELs 4952 is optically transferred to the fiber distribution module 4953, where a portion of the laser light is optically transferred to a fiber connector 4960 for analysis in a main electronic board 4970. The fiber connector 4960 may connect a plurality of optical fibers from the fiber distribution module 4953 to the fiber connector module 4960. Another portion of the laser light is optically transferred to an optical path distance correction (OPD) module 4940 and ultimately to the free space retinal thickness optics 4910-1 for delivery to a user's eye and measurement of the user's eye with a portion of the measurement arm of the Mach-Zender interferometer. For example, the OPD correction module 4940 may comprise a peripheral board 4943 that is controlled by the main electronic board 4970 to actuate a motorized stage 4942 to change the optical path distance between the user's eye, a coupler of the Mach-Zender interferometer and the one or more VCSELs 4952. The OPD correction module 4940 may also comprise a fiber collimator 4941 that collimates the laser light from the VCSELs 4952 before delivery to the user's eye, and the fiber collimator can be translated with the OPD correction module 4940.

A controller interface 4930 may be used to receive user inputs to control the binocular OCT measurement system. The controller interface may comprise a first controller interface 4930-1 and a second controller interface 4930-2. The controller interface 4930 may comprise a trigger button mechanism that allows a user to initiate a sequence of steps to align the eye and measure the retina as described herein. Alternatively or in combination, the device may be configured with an auto-capture function, such that the data is automatically acquired when the device is aligned to the eye within appropriate tolerances.

Additionally, the binocular OCT device 4900 may comprise a scanner module 4990 that scans the laser light from the one or more VCSELs 4952 in a pattern (e.g., a stop and go scan pattern, a star scan pattern, a continuous scan pattern, a Lissajous scan pattern, or a flower scan pattern (rose curve)). For example, a peripheral board 4991 of the scanner module 4990 may be communicatively coupled to the main electronic board 4970 to receive control signals that direct the scanner module 4992 to scan the pulsed laser light from the VCSELs 4952 in a pattern to perform an optical coherence tomography (OCT) on the user's eye. The scanning module 4990 may comprise a sealing window 4992 that receives the laser light from the fiber collimator 4941 and optically transfers the laser light to a free space two-dimensional scanner 4993, which provides the scan pattern of the laser light. The two-dimensional scanner may comprise a scanner as described herein, such as a two-axis galvanometer, or a two axis electro-static scanner, for example. When present, the sealing window 4992 may be used to keep the internal components of the binocular OCT device 4900 free of dirt and/or moisture. The laser light is then optically transferred to relay optics 4994 such that the scanned laser light can be input to the user's eye via the free space RT optics 4910-1. In this regard, the scanned laser light may be transferred to a hot mirror 4913 such that infrared light may be reflected back towards the hot mirror, the scanning mirror and focused into an optical fiber tip coupled to the collimation lens. The hot mirror 4913 generally transmits visible light and reflects infrared light, and may comprise a dichroic short pass mirror, for example.

The scanner and associated optics can be configured to scan any suitably sized region of the retina, such as regions comprising the fovea. In some embodiments, the scanner is configured to scan the retina with a scanning pattern, such as a predetermined scanning pattern in response to instructions stored on a processor such as the controller. For example, the scanner can be configured to scan the retina over an area comprising a maximum distance across within a range from about 1.5 to 3 mm, for example. The scanning region of the retina may comprise an area larger than maps of retinal thickness in order to account for slight errors in alignment, e.g. up to 0.5 mm in the lateral positioning of the eye in relation to the OCT system, for example in order to compensate for alignment errors, e.g. by aligning the map based on the measured position of the eye. The size of the OCT measurement beam on the retina can be within a range from about 25 microns to about 75 microns. In some embodiments, the mirror is moved with a continuous trajectory corresponding to a scan rate on the retina within a range from about 10 mm per second to about 200 mm per second, and the scan rate can be within a range from about 50 mm per second to about 200 mm per second. The displacement of the beam during an A-scan can be within a range from about 2 to 10 microns, for example. The beams for each of a plurality of A-scans can overlap. In some embodiments, the mirror moves continuously with one or more rotations corresponding to the trajectory of the scan pattern and the swept source VCSEL turns on and off with a suitable frequency in relation to the size of the beam and the velocity of the beam on the retina. In some embodiments each of the plurality of A-scans overlaps on the retina during at least a portion of the scan pattern.

In embodiments where the one or more VCSELs comprises a plurality of VCSELs, the plurality of VCSELs can be sequentially scanned for each A-scan, such that the measurement beams from each of the plurality of VCSELs overlaps on the retina with a prior scan. For example, each of the sequentially generated beams from each of the plurality of VCSELs from a first A-scan can overlap with each of the sequentially generated beams from each of the plurality of VCSELs from a second A-scan along the trajectory.

As described herein, the binocular OCT device 4900 may comprise an IPD adjustment via the components 4905-1 and/or 4905-2. These components may be communicatively coupled to a manual translation stage IP adjustment module 4982 that perform the actuation of the free space optics modules 4910-1 and 4910-2, so as to change a separation distance between the free space optics modules and adjust the IPD.

The main electronic board 4970 may comprise a variety of components. For example, a photodetector 4972 may be used to receive laser light directed from the VCSELs 4952 through the fiber connector 4960 as well interfering light reflected from the user's eye. The fiber connector 4960 may comprise a module 4961 that couples a plurality of optical fibers, for example four optical fibers, to a plurality of detectors, for example five detectors. The fiber connector 4960 may also comprise an interferometer clock box 4962 (e.g. an etalon) that may be used in phase wrapping light reflected back from the user's eyes, as shown and described herein. Once received by the photodetectors 4972, the photodetectors 4972 may convert the light into electronic signals to be processed on the main electronic board 4970 and/or another processing device. The plurality of photo detectors may comprise two detectors of a balanced detector pair coupled to the fiber Mach-Zender interferometer, a clock box detector, and a pair of power measurement detectors, for example.

The main electronic board 4970 may comprise a communication power module 4973 (e.g., a Universal Serial Bus, or "USB") that can communicatively couple the binocular OCT device 4900 to another processing system, provide power to the binocular OCT device 4900, and/or charge a battery of the binoculars OCT device 4900. Of course, the binocular OCT device 4900 may comprise other modules that may be used to communicate information from the binocular OCT device 4900 to another device, including for example, Wi-Fi, Bluetooth, ethernet, FireWire, etc.

The main electronic board 4970 may also comprise VCSEL driving electronics 4971 which direct how and when the VCSELs 4952 are to be fired towards the user's eyes. Other components on the main electronic board 4970 comprise an analog block 4974 and a digital block 4975 which may be used to process and/or generate analog and digital signals, respectively, being transmitted to the binocular OCT device 4900 (e.g., from an external processing system), being received from various components within the binocular OCT device 4900, and/or being received from various components within the binocular OCT device 4900. For example, the peripheral feedback button 4932 may generate an analog signal that is processed by the analog block 4974 and/or digital clock 4975, which may in turn generate a control signal that is used to stimulate the motorized stage module 4942 via the peripheral board 4943. Alternatively, or additionally, the analog block 4974 may process analog signals from the photodetectors 4972 such that they may be converted to digital signals by the digital block 4975 for subsequent digital signal processing (e.g., FFTs, phase wrapping analysis, etc.).

Figure 6:
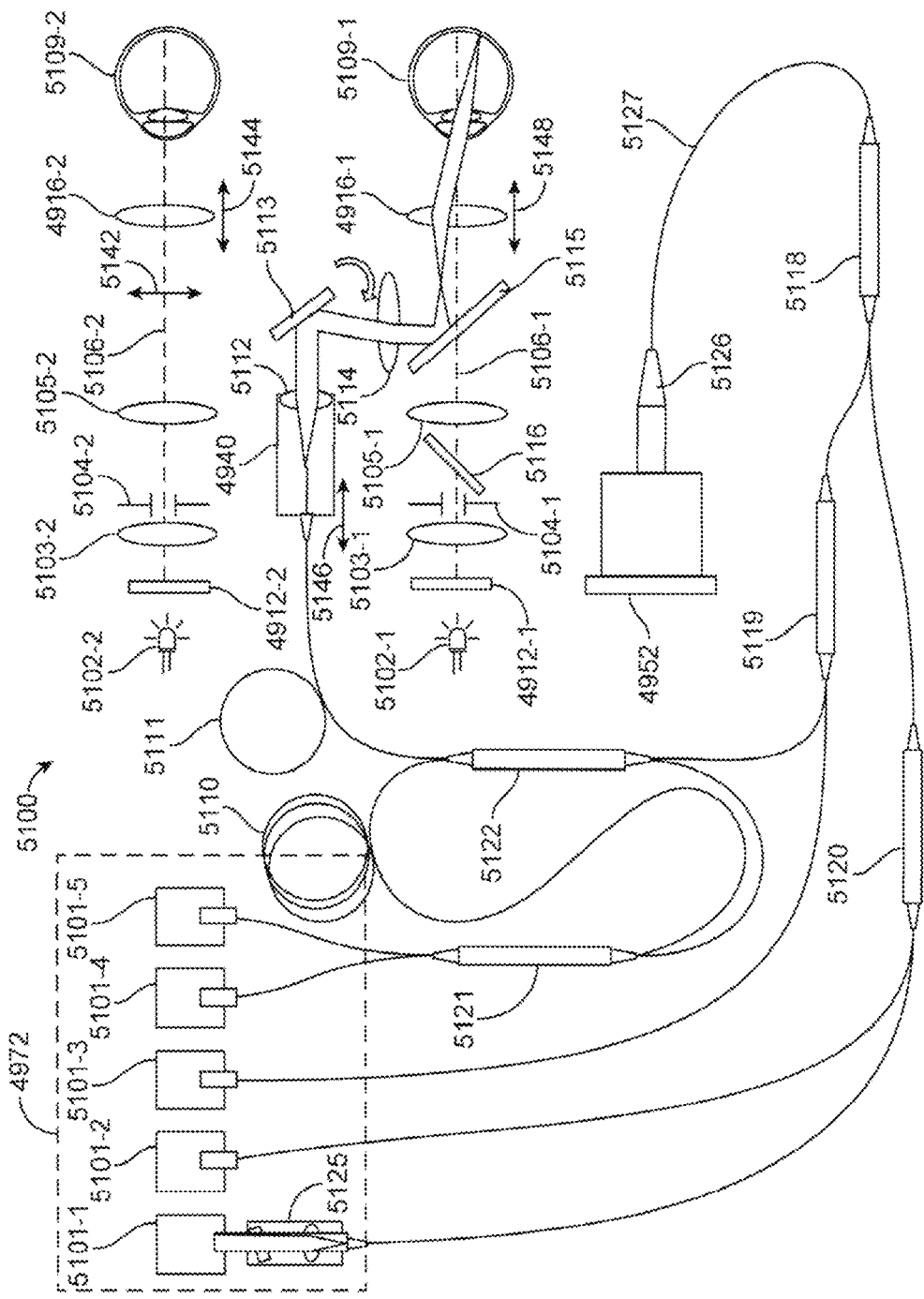
FIG. 6 shows a schematic of an optical configuration that may be implemented with the OCT binocular, in accordance with some embodiments.

FIG. 6 shows a schematic of an optical configuration 5100 that may be implemented with the OCT binocular 4900, in accordance with some embodiments. The optical configuration 5100 comprises one or more VCSELs 4952 that are fiber coupled via an optical coupler 5126. As discussed above, the one or more VCSELs 4952 may be swept over a range of wavelengths when fired. For embodiments with a plurality of VCSELs 4952, the wavelengths may partially overlap a wavelength sweep range of another VCSEL 4952 in the plurality so as to increase in overall sweep range of the VCSELs 4952. In some instances, this overall sweep range is centered around approximately 850 nm. The laser light from the one or more VCSELs 4952 is propagated through the fiber coupler 5126 to a fiber optic line 5127, where another optical coupler 5118 splits a portion of the optical energy from the one or more VCSELs 4952 along two different paths.

In the first path, approximately 95% of the optical energy is optically transferred to another optical coupler 5119 with approximately 5% of the optical energy being optically transferred to an optical coupler 5120. In the second path, the optical energy is split yet again via an optical coupler 5120. In this regard, approximately 75% of the optical energy from the optical coupler 5120 is transferred to a phase correction detector 5101-1 through an interferometer such as a Fabry Perot interferometer comprising an etalon. The etalon and detector may comprise components of an optical clock 5125. The optical clock 5125 may comprise a single etalon, for example. The etalon may comprise substantially parallel flat surfaces and be tilted with respect to a propagation direction of the laser beam. The surfaces may comprise coated or uncoated surfaces. The material may comprise any suitable light transmissive material with a suitable thickness. For example, the etalon may comprise a thickness within a range from about 0.25 mm to about 5 mm, for example within a range from about 0.5 mm to about 4 mm. The reflectance of the etalon surfaces can be within a range from about 3% to about 10%. The etalon can be tilted with respect to the laser beam propagation direction, for example tilted at an angle within a range from about 5 degrees to about 12 degrees. The finesse of the etalon can be within a range from about 0.5 to about 2.0, for example, for example within a range from about 0.5 to 1.0. The etalon may comprise any suitable material such as an optical glass. The thickness, index of refraction, reflectance and tilt angle of the etalon can be configured to provide a substantially sinusoidal optical signal at the clock box detector. The finesse within the range from about 0.5 to 2.0 can provide substantially sinusoidal detector signals that are well suited for phase compensation as described herein, although embodiments with higher finesse values can be effectively utilized.

In some embodiments, the clockbox may comprise a plurality of etalons. The approach can be helpful in embodiments wherein the one or more VCSELs comprises a plurality of VCSELs, and the plurality of etalons provides additional phase and clock signal information. For example, the clockbox may comprise a first etalon and a second etalon arranged so that light is transmitted sequentially through the first etalon and then the second etalon, e.g. a series configuration, which can provide frequency mixing of the clock box signals and decrease the number of detectors and associated circuitry used to measure phase of the swept source. Alternatively, the plurality of etalons can be arranged in a parallel configuration with a plurality of etalons coupled to a plurality of detectors.

The phase correction detector 5101-1 may use the light signals from the optical clock 5125 to correct the phase of light reflected from a user's eyes 5109-1 by matching the phases of the one or VCSELs 4952 via phase wrapping of the light from the one or more VCSELs 4952 as described herein. The remaining 25% of the optical energy from the optical coupler 5120 may be optically transferred to a detector 5101-2 for optical safety. For instance, the detector 5101-2 may be used to determine how much optical energy is being transferred to the user's eye 5109-1 or 5109-2, depending on the orientation of the device. If the binocular OCT device 4900 determines that the detector 5101-2 is receiving too much optical energy that may damage the user's eyes, then the binocular OCT device 4900 may operate as a "kill switch" that shuts down the VCSELs 4952. Alternatively, or additionally, the binocular OCT device 4900 may monitor the detector 5101-2 to increase or decrease the optical energy from the VCSELs 4952 as deemed necessary for laser safety and/or signal processing. The OCT device may comprise a second safety detector 5101-3 to provide a redundant measurement for improved eye safety.

The optical energy transferred to the optical coupler 5119 (e.g., approximately 95% of the optical energy from the one or more VCSELs 4952) is also split along two paths with approximately 99% of the remaining optical energy being optically transferred along a fiber to an optical coupling element 5122 and with approximately 1% of the remaining optical energy also being optically transferred to a detector 5101-3 for laser safety of the binocular OCT device 4900. The portion of the optical energy transferred to the to the optical coupler 5122 may be split by the optical coupler 5122 between two optical path loops 5110 and 5111 of the Mach-Zender interferometer, approximately 50% each, for example. The optical path loop 5110 may comprise a reference arm of the interferometer and provide a reference optical signal for the retinal thickness measurement of the user's eye 5109-1 (e.g., the measurement signal reflected from the user's retina through the optical path loop 5111).

The portion of the optical energy transferred through the optical loop 5111 is transferred to the user's left eye 5109-1 along the measurement arm of the Mach-Zender interferometer. For instance, the optical energy being transferred to the user's eye 5109-1 may pass through the OPD correction module 4940 to perform any optical path distance corrections appropriate to the interferometer of the binocular OCT device 4900. This light may then be scanned across the user's eye 5109-1 via a scanning mirror 5113 of the scanner module 4990 to measure the retinal thickness of the user's eye 5109-1 while the user's eye 5109-1 is fixated on a fixation target 4912-1 (e.g., along a fixation path 5106-1).

The fixation target 4912-1 can be back illuminated with LED 5102-1, and light may be propagated along the optical path 5106-1 through optical elements 5103-1 and 5105-1 and the dichroic mirror 5115, comprising a hot mirror. In some instances, the target of fixation may also include an illumination stop 5104 so as to provide relief to the user's eye 5109-1 while fixating on the target.

The light impinging the user's retina of the eye 5109-1 may be reflected back along the path established by the OPD correction module 4940, the scanning mirror 5113, the focusing element 5114, the dichroic mirror 5115, and the optical element 4916-1, through the optical loop 5111, and back to the optical coupler 5122. In this instance, the optical coupler 5122 may optically transfer the reflected optical energy to an optical coupler 5121 which may couple the reflected optical energy with the optical energy that was split into the optical loop 5110. The optical coupler 5121 may then optically transfer that optical energy to the balanced detector's 5101-4 and 5101-5 such that a retinal thickness measurement can be performed. In doing so, the optical coupler 5121 may split that optical energy to approximately 50% to each of the detectors 5101-1 and 5101-4, such that the interference signals arrive out of phase on the balanced detectors.

The light may be focused through a plurality of optical elements 5112 and 5114, being directed to the user's eye 5109-1 via a dichroic mirror 5115 and focused on the user's retina via the optical element 4916-1. The light from the scanning mirror 5113 and the light reflected from the user's eye 5109 are both shown as reflecting off the dichroic mirror 5115, which may comprise hot mirror 4913 configured to generally reflect infrared light and transmit visible light.

As can be seen in this example, the user's right eye 5109-2 does not receive any optical energy from the one or more VCSELs 4972 with the orientation shown. Rather, the user's right eye 5109-2 is used for binocular fixation with the target 4912-2, which can be back illuminated with another LED 5102-2. The target 4912-2 can be of similar size and shape to target 4912-1 and be presented to the eye with similar optics, so as to provide binuclear fixation. In this regard, the user's right eye 5109-2 may also fixate on the target 4912-2 along an optical path 5106-2 through the optical elements 4916-2, 5105-2, 5103-2, and the illumination stop 5104-2, which comprises similar optical power, separation distances and dimensions to the optics along optical path 5106-1.

The binocular OCT system 4900 can be configured to move optical components to a customized configuration for the user being measured. Lens 4916-1 can be adjusted along optical path 5106-1 in accordance with the refraction, e.g. eyeglass prescription of the eye being measured. Lens 4916-1 can be moved under computer, user or other control to adjust lens 4916-1 to bring the fixation target 4912-1 into focus and to focus the measurement beam of the OCT interferometer on the user's retina. For example, the lens can be translated as shown with arrow 5146. Lens 4916-2 can be moved under computer, user or other control to adjust lens 4916-2 to bring the fixation target 4912-2 into focus on the user's retina. For example, the lens can be translated as shown with arrow 5144. The OPD correction module 4940 can be translated axially toward and away from mirror 5113 as shown with arrows 5146. The OPD correction module 4940 can be moved under computer control to appropriately position the optical path difference between the measurement arm and the reference arm for the user's eye being measured. The interpupillary distance can be adjusted by translating the optical path 5106-2 toward and away from optical path 5106-1.

The free space optics module 4910-2 may comprise one or more components along optical path 5106-2, such as the LED 5101-2, the fixation target 4912-2, lens 5103-2, aperture 5104-2, lens 5105-2, or lens 4916-2. The free space optics module 4910-2 can be translated laterally toward and away from the optical components located along optical path 5106-1 to adjust the inter pupillary distance as shown with arrow 5142. The free space retinal thickness optics module 4910-1 may comprise one or more components located along optical path 5106-1, such as the LED 5102-1, the fixation target 5103-1, the aperture 5104-1, the mirror 5116, the lens 5105-1, the mirror 5115, or lens 4916-1. The OPD correction module 5146 may comprise the optical fiber of the measurement arm of the interferometer, and lens 5112 to substantially collimate light from the optical fiber and to focus light from the retina into the optical fiber.

Figure 7:
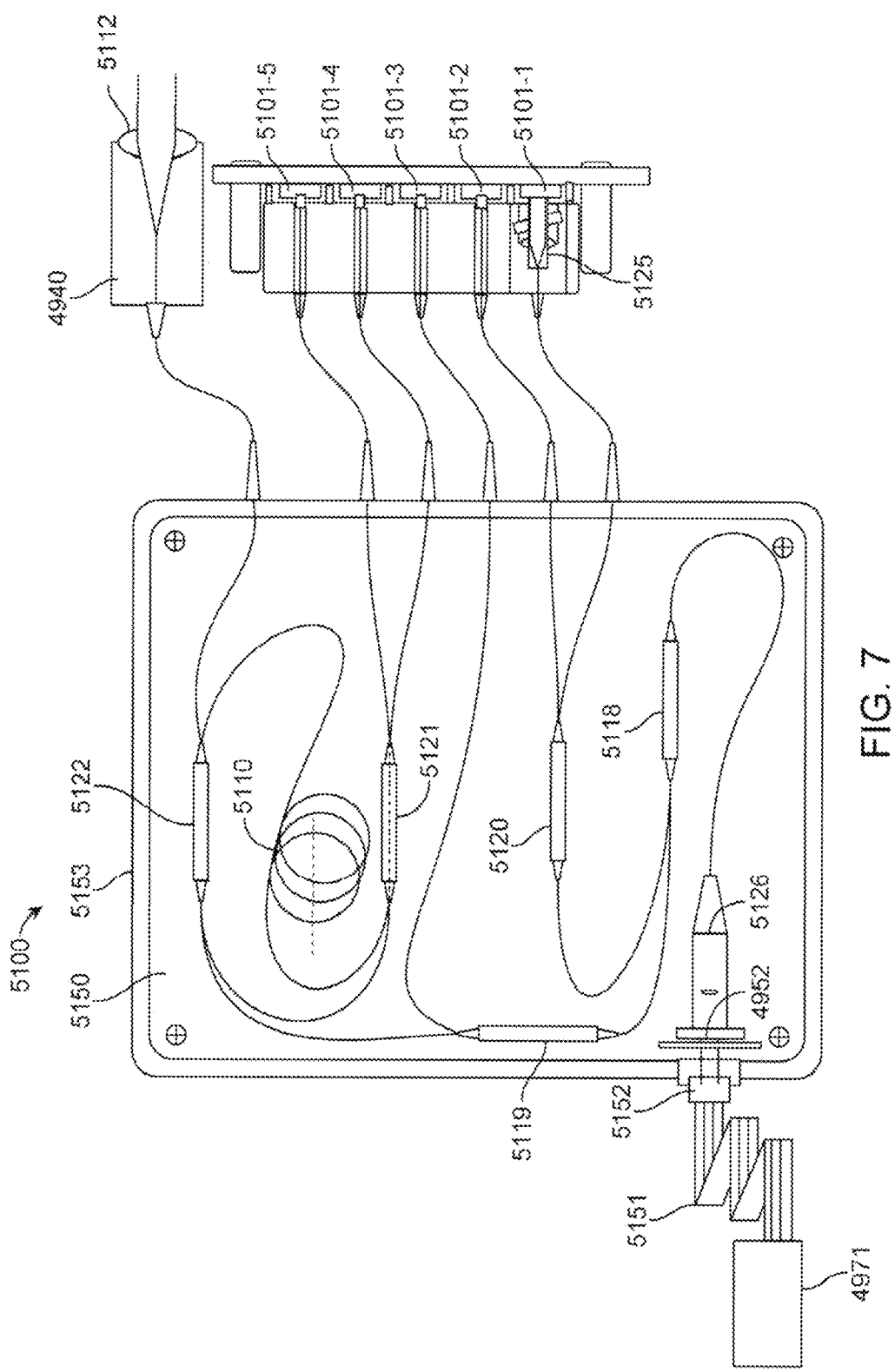
FIG. 7 shows a block diagram of the optical configuration configured on an optical layout board, in accordance with some embodiments.

FIG. 7 shows a block diagram of the optical configuration 5100 configured on an optical layout board 5150, in accordance with some embodiments. For example, the binocular OCT device 4900 may be configured with a plurality of layers extending approximately along planes, each of which layers may be configured to perform a particular function. In this instance, the optical layout board 5150 provides a support for the optical configuration 5100, which can be used to decrease vibrations of the optical components. The optical board 5150 may comprise a plurality of components enclosed within a housing of a fiber optics module as described herein. The plurality of components enclosed within the housing 5153 and supported on the board, may comprise one or more of coupler 5118, coupler 5119, coupler 5120, coupler 5121, coupler 5122, reference arm comprising optical fiber 5110, and any combination thereof. The one or more VCSELs 4952 may be enclosed within the housing. The plurality of optical fibers extending from coupler 5120 can extend through the housing to the appropriate detector, for example to couple to clock box detector 5101-1 and safety detector 5101-2. The optical fiber extending from coupler 5119 can be coupled to a second safety detector 5101-3 and extend though housing 5153. A second optical fiber extending from coupler 5119 can be coupled to the interferometer to measure the sample with optical coupler 5122. The optical fiber portion of the sample measurement arm may extend from coupler 5122 and through the housing 5153 to the optical path difference correction module 4940, for example.

The printed circuit board may provide a support layer extending along an electronics plane in which some processing devices (e.g., the main electronic board 4970 including the driving electronics 4971) could couple to the optical layout board 5150 through a cable 5151 that connects to a connector 5152 configured with the optical layout board 5150 in order to drive one or more VCSELs 4952.

Figure 8:
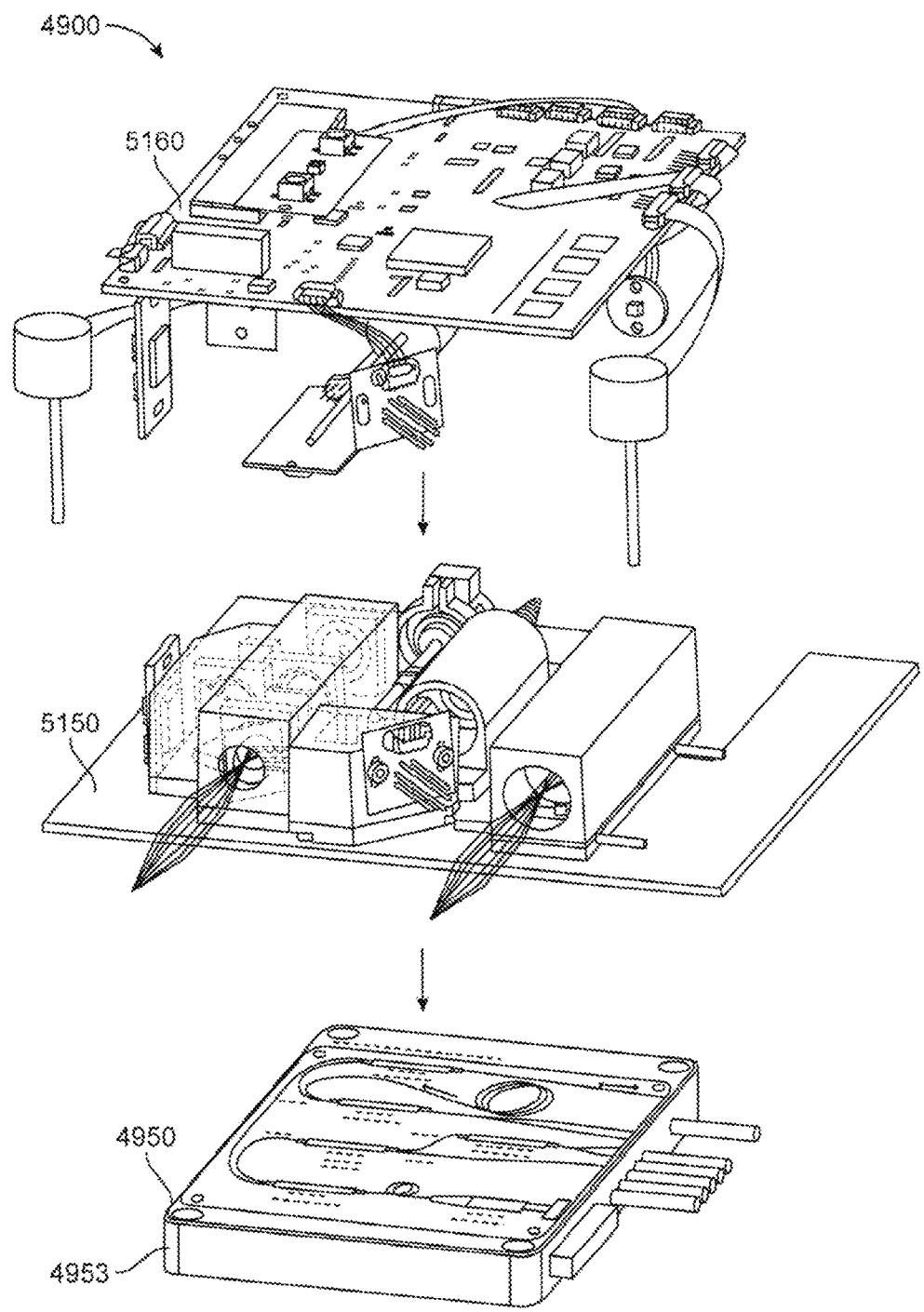
FIG. 8 shows a perspective view of a modular binocular OCT, in accordance with some embodiments.

FIG. 8 shows a perspective view of a modular embodiment of the binocular OCT 4900, in accordance with some embodiments. For instance, the main electronic board 4970 of the binocular OCT 4900 may be implemented as a printed circuit board (PCB) 5160 that is mounted to a housing 4953 enclosing optical components on the optical layout board 5150. The PCB 5160 may provide the power and electronics to control the optical configuration 5100 of the optical layout board 5150. The PCB 5160 may also include or be communicatively coupled to peripheral boards 4932-1, 4932-2, 4943, 4914-1, and 4914-2. The binocular OCT device 4900 may also comprise free space optics modules that are mounted on the optical layout board 5150 and communicatively couple to the main electronic board 4970. The free space optics modules mounted on the optics board may comprise one or more of module 4910-1, module 4910-2, or OPD correction module 4940 as described herein. The free space module 4910-2 can be configured to move in relation to optical layout board 5150 to adjust the inter pupillary distance. The OPD correction module can be configured to move relative to optical layout board 5150.

The interferometer module 4950 may comprise the couplers of the optical fibers as descried herein and the one or more VCSELs 4952. The main electronic board 4970 or one of the peripheral boards may comprise the electronics that drive the VCSELs 4952. The one or more VCSELs 4952 being optically coupled to the optical fibers on the optical layout board 5150, propagate laser light to the optical fibers on the optical layout board 5150. The laser light reflected from the user's eye 4910-1 can be propagated to the PCB 5160 where the photodetector 4972 detects the reflected laser light and converts the light to an electronic analog signal for processing by the analog block 4974.

In some embodiments, the optical layout board 5150 provides damping to the binocular OCT 4900. For instance, if the binocular OCT 4900 were to be dropped, a damping mechanism configured with the optical layout board 5150 may compensate for any oscillatory effects on impact of the binocular OCT 4900 and protect the components thereof (e.g., the optical layout board 5150, the PCB 5160, interferometer module 4950, and the components of each). The mounting plate 5150 may comprise similar damping mechanisms.

Figure 9:
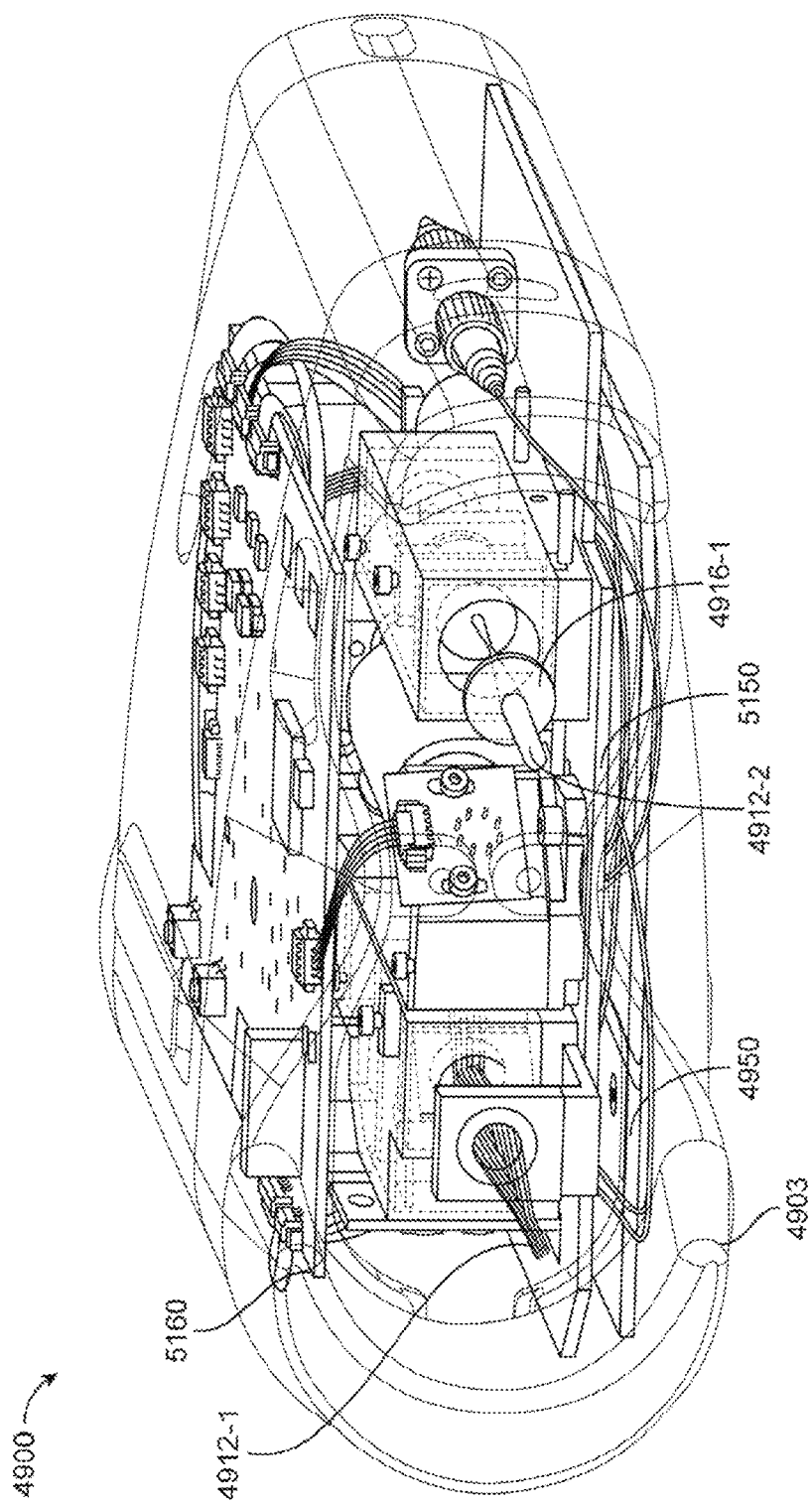
FIG. 9 shows a perspective/cut-away view of the binocular OCT device, in accordance with some embodiments.

FIG. 9 shows a perspective/cut-away view of the binocular OCT 4900, in accordance with some embodiments. In this view, the optical layout board 5150, the PCB 5160, and the interferometer module 4950 are mechanically coupled together in a compact form configured within the housing 4903 of the binocular OCT 4900. As can be seen in this view, the fixation targets 4912-1 and 4912-2 (e.g., LED light) are visible to the user through the lenses 4916-1 and 4916-2, respectively, when the user places the binocular OCT 4900 proximate to the user's eyes. Laser light from the VCSELs propagates along a portion of the same optical path as the fixation target 4912-1. Thus, when the user gazes on the fixation targets 4912-1 and 4912-2, the laser light from the one or more VCSELs as described herein are operable to propagate through the user's eye and reflect back to the optical layout board 5150 for subsequent processing to determine the user's retinal thickness.

Figure 10:
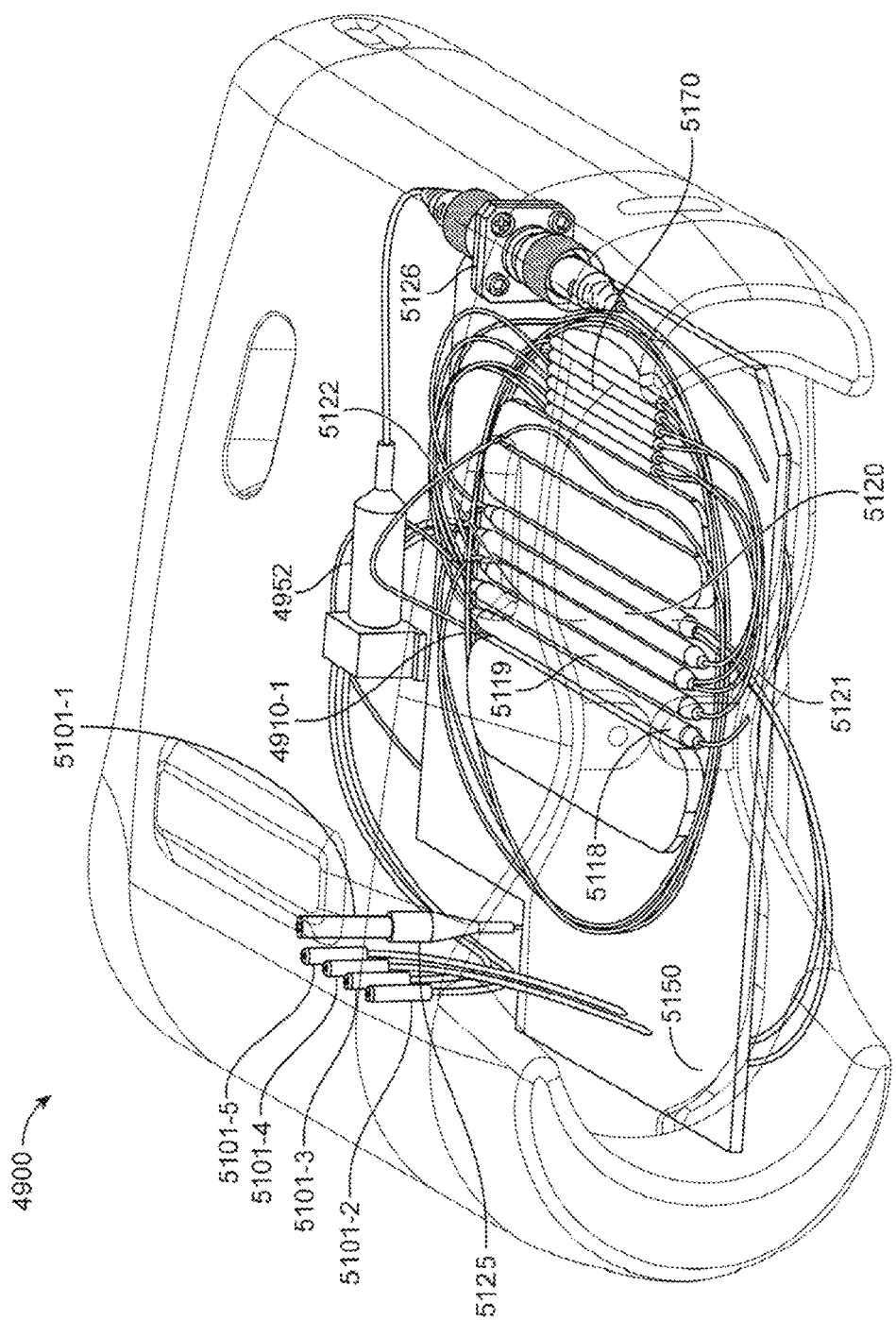
FIG. 10 shows another perspective/cut-away view of the binocular OCT device, in accordance with some embodiments.

FIG. 10 shows another perspective/cut-away view of the binocular OCT 4900, in accordance with some embodiments. In this view, the optical layout board 5150 is illustrated to show the configuration of the one or more VCSELs 4952, the fiber coupler 5126, the detector's 5105-1-5105-5, the Fabry Perot optical clock 5125, and the optical couplers 5118-5122. The optical layout board 5150 may also comprise splices 5170.

Figure 11:
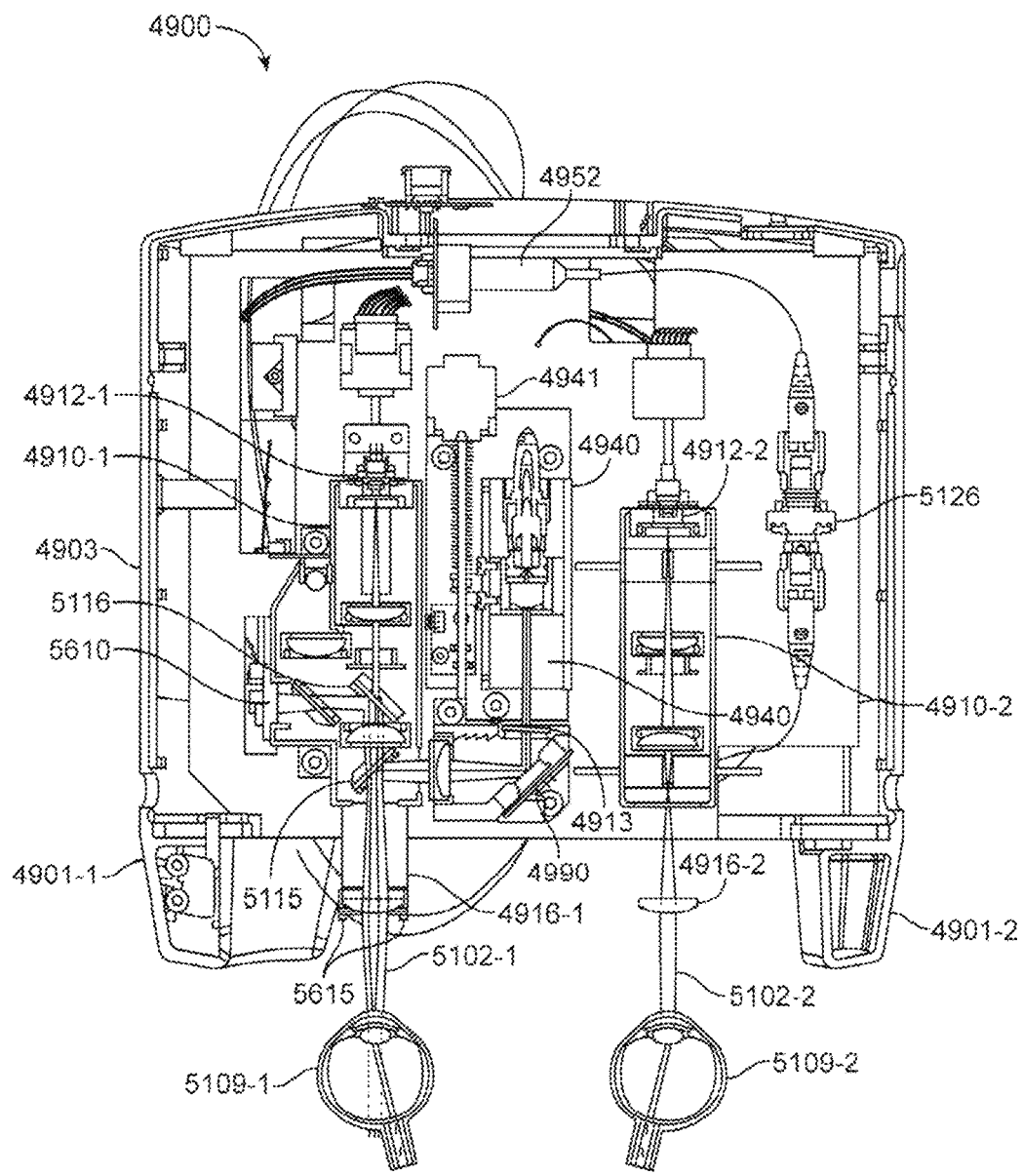
FIG. 11 shows an overhead/cut-away view of the binocular OCT device comprising an eye position sensor, in accordance with some embodiments.

FIG. 11 shows the binocular OCT system 4900 comprising an eye position sensor, in accordance with some embodiments. FIG. 11 shows an overhead/cut-away view of the binocular OCT 4900 comprising an eye position sensor 5610, in accordance with some embodiments. The eye position sensor 5610 may comprise one or more of an array sensor, a linear array sensor, a one dimensional array sensor, a two-dimensional array sensor, a complementary metal oxide (CMOS) two-dimensional array sensor array sensor, a quadrant detector or a position sensitive detector. The eye position sensor 5610 can be combined with a lens to form an image of the eye on the sensor, such as a Purkinje image from a reflection of light from the cornea of the eye. The eye position sensor can be incorporated into any of the embodiments disclosed herein, such as the binocular OCT system described with reference to FIGS. 4 to 10.

In the view shown, the optical configuration 5100 is mounted on the optical layout board 5150 above the fiber-optic couplings (e.g., the fiber loops 5110 and 5111 of FIG. 6) and the optical couplers 5118-5122, and other fiber components as described herein. Thus, the one or more free space optical components as described herein may be optically coupled to the fiber components thereunder.

As shown, the free space optics modules 4910-1 and 4910-2 are generally aligned with the user's eyes 5109-1 and 5109-2, respectively. The distance between the free space optics modules 4910-1 and 4910-2 may be adjusted according to the user's IPD. In some embodiments, this adjustment is maintained for the user while the binocular OCT 4900 is in the user's possession. For example, the user may be a patient using the binocular OCT 4900 for home use over a certain period of time. So as to ensure that a correct retinal thickness is measured while in the user's possession, the binocular OCT 4900 may prevent the user from adjusting the IPD. Similarly, the binocular OCT 4900 may also prevent the user from adjusting the OPD via the OPD correction module 4940.

As can be seen in this view (FIG. 11), the fixation targets 4912-1 and 4912-2 (e.g., LED light targets) pass through various optical elements of their respective free space optics modules 4910-1 and 4910-2. The OPD correction module 4940 receives the laser light from the one or more VCSELs 4952 and directs light toward the scanning mirror 4990 as described herein. Light from the scanning mirror 4990 passes through a lens and is reflected by a dichroic mirror 5115 to the user's eye 5109-1 through the lens 4916-1.

In some embodiments, the OCT measurement beam remains substantially fixed relative to the position sensor at each of the plurality of positions of the fixation target.

In some embodiments, the retinal thickness map comprises a plurality of regions corresponding to the plurality of positions of the fixation target.

In some embodiments, the retinal thickness map comprises from 5 to 20 regions and the plurality of locations of the fixation target comprises from 5 to 20 regions.

In some embodiments, the OCT system comprises a scanner to scan the OCT beam to a plurality of positions on a patient's retina for each of the plurality of positions of the fixation target. For example, the scanner can be configured to scan an area of the retina with the plurality of retinal positions for each of the plurality of fixation target positions, and the area of the retina scanned with each of the plurality of fixation target positions is less than an area of the one or more of retinal thickness map or the retinal image.

In some embodiments, the OCT measurement beam is transmitted to the scanning mirror mounted on a piezo driven motor in order to compensate for the optical path distance. For example, the hot mirror configured to reflect the OCT measurement beam and transmit the fixation target can be configured to translate in order to adjust the optical path difference while the position of the XYZ translation stage remains substantially fixed. In some embodiments, the translation of the mirror will reflect the OCT measurement beam to adjust the OPD while the path of the transmitted light remains substantially unaltered, such as the path of the light from the fixation target and optionally light transmitted through the mirror to the position sensor.

In some embodiments, the OCT beam is routed through a micromirror/microlens assembly, in which both direction and OPD can be adjusted. In some embodiments, the beam radius may also be varied. The micro-optics assembly may be mounted on a set of linear drives, including piezo drives with submicron resolution. Such drives are commercially available from DTI motors as described on the Internet at dtimotors.com.

Such a system may rely on a decreased driving force, so that a driving force of 1N may be sufficient, in accordance with some embodiments.

In some embodiments the driving force is within a range from 0.5 Newtons (N) to 2.5 N, and a resolution does not exceed 0.5 microns. In some embodiments, the response time is 1 mm per 0.1 sec or faster. This lens assembly can be controlled with a processor such as a microcontroller or an FPGA, so as to increase the signal-to-noise ratio as described herein. In some embodiments, the lens assembly is configured to dither the OCT measurement beam on the retina.

As described, the disclosed OCT system includes a scanner that can be controlled to cause a measurement beam to move in a scan pattern on a patient's retina. The scan pattern may be one of various types, including a stop and go scan pattern, a star scan pattern, a continuous scan pattern, a Lissajous scan pattern, or a flower pattern, sometimes referred to as a rose curve. As will be described in further detail, the flower pattern or rose curve may be used to generate measurement data that can be processed to generate data that represents data that would be obtained from a different scan pattern. Further, the flower pattern or rose curve may be used to generate measurement data that can be processed to generate interferometric data that improves the ability to detect fluid or pockets of fluid in regions of the retina.

Figure 12A:
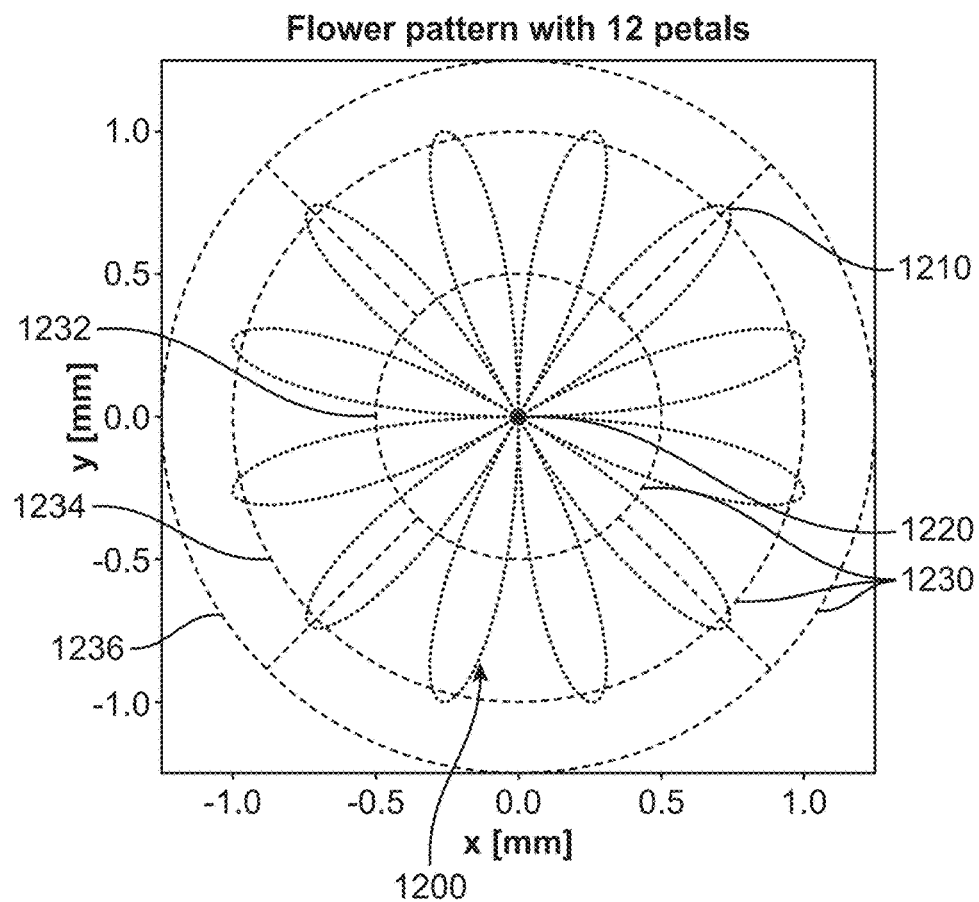
FIG. 12A shows an example of a scan pattern (termed a "flower" pattern herein) that may be used to collect OCT data, in accordance with some embodiments.

FIG. 12A shows an example of a scan pattern (termed a "flower" scan pattern herein) that may be used to collect OCT data, in accordance with some embodiments. The scan pattern 1200 shown in the figure is also referred to as a rose curve, where a rose curve is a polar coordinate representation of a sinusoid. The flower scan pattern 1200 comprises a plurality of lobes 1210 or petals, with one end of each lobe being connected to and extending radially outward from a central point or location 1220. The flower pattern shown in the figure has 12 lobes or petals, although a different number may be present in a scan pattern.

The figure shows a superposition of the scan pattern on a patient's eye and indicates several regions of tissue of the eye, such as the retinal tissue. The three concentric rings or annular regions 1230 (shown by dashed lines) in the figure represent different zones or regions of a retina of a patient's eye. In some embodiments, the innermost ring 1232 represents at least a portion of the fovea region of a patient's eye, the middle ring 1234 represents the macular region of a patient's eye, and the outermost ring 1236 represents a region outside the fovea. The sector or region in between the innermost ring 1232 and the middle ring 1234 is divided into 4 zones in the figure. Similarly, the sector or region in between the middle ring 1234 and the outermost ring 1236 is divided into 4 zones in the figure. In some embodiments, the plurality of zones comprises a total of 9 identified zones or regions of a patient's retina. In some embodiments, the innermost ring has a diameter of about 1 mm and contains the fovea, which may have a diameter of about 0.35 mm. In some embodiments, the middle ring has a diameter of about 2 mm and contains the macula, which may have a diameter of about 1.5 mm. In some embodiments, the outermost ring has a diameter of about 2.5 mm and represents the retinal region outside the macula.

In the example scan pattern shown in the figure, each dot along the scan trajectory represents a location on the retina at which a measurement is made and data is collected. Note that the density of measurements (i.e., the spacing between the measurement points or dots) varies along different regions or sections of the trajectory. As shown in the example, the density of measurements is less for the portion of a lobe that lies within the innermost ring 1232. The density of measurement points increases for the portion of the scan pattern that lies outside the innermost ring 1232, increasing for the portion between rings 1232 and 1234, and further increasing for the portion at the end or tip of a lobe, which in the example, lies outside the middle ring 1234. Thus, in this example, the density of measurement and data collection points varies along the scan. In some embodiments, the density of measurement points along a scan pattern may be controlled by varying the scan speed of the mirror and the geometry of the scan pattern generated by the scanning mirror, while maintaining the same A-Scan acquisition rate. Note that each lobe 1210 comprises a substantially continuous scan pattern with an unscanned region inside the lobe or scan path of the measurement beam. As indicated by the measurement points and the variation in density of those points, the measurement beam and/or the sampling of data is not continuous and is instead modulated (turned on and off) during the scanning process.

Figure 12B:
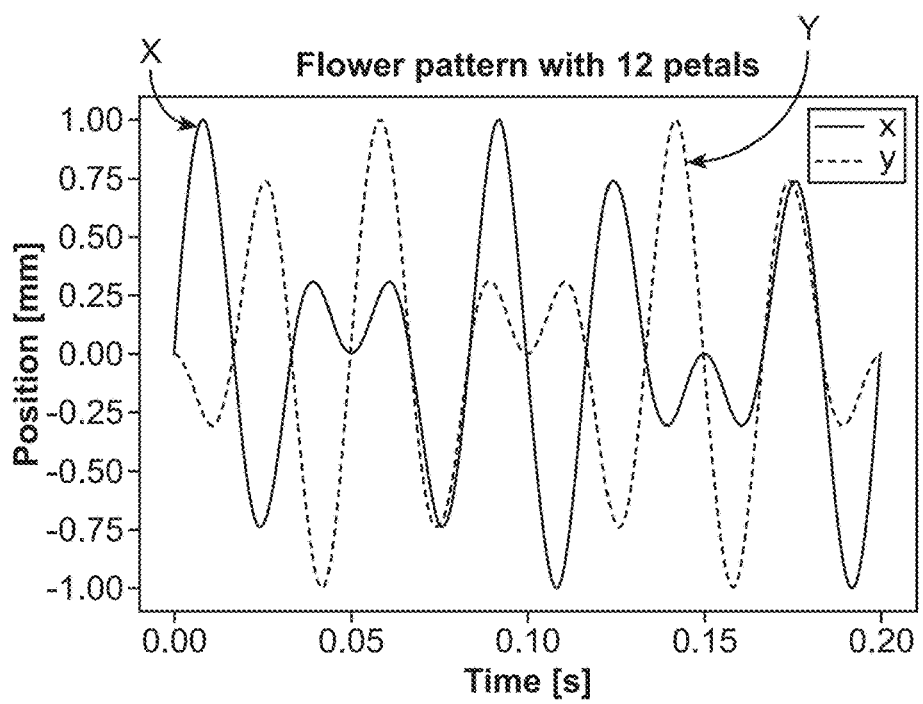
FIG. 12B shows the position of the measurement beam in the x and y directions as a function of time for the scan pattern of FIG. 12A, in accordance with some embodiments.

FIG. 12B shows the position of the measurement beam on the retina in the x and y directions as a function of time for the scan pattern of FIG. 12A, in accordance with some embodiments. The figure shows the X and Y position of a measurement beam as a function of time as a mirror in a scanner is used to move the beam on a patient's retina. The mirror may be caused to move by applying a voltage or current waveform to one or more actuators, such as a microelectromechanical (MEMs) device. In some embodiments, the mirror may be caused to move by application of an electrostatic force. The electrostatic force may be provided by one or more capacitors.

In some embodiments, the position or orientation of the mirror may be caused to move by application of an electromagnetic force. In some embodiments, the electromagnetic force may be provided by one or more of a galvanometer, an electrostatic transducer, or a piezo electric transducer.

The waveform of the voltage or current applied to an actuator or other element operating to move a scanner mirror may vary from the form shown in the figure as a result of non-linearities between an applied voltage or current and the resulting motion of the scanner mirror in a direction along or about one of its axes. A calibration process may be used to better determine the type of input signal or waveform that can cause a scanner mirror to move in a manner that will produce a desired scan pattern.

Figure 12C:
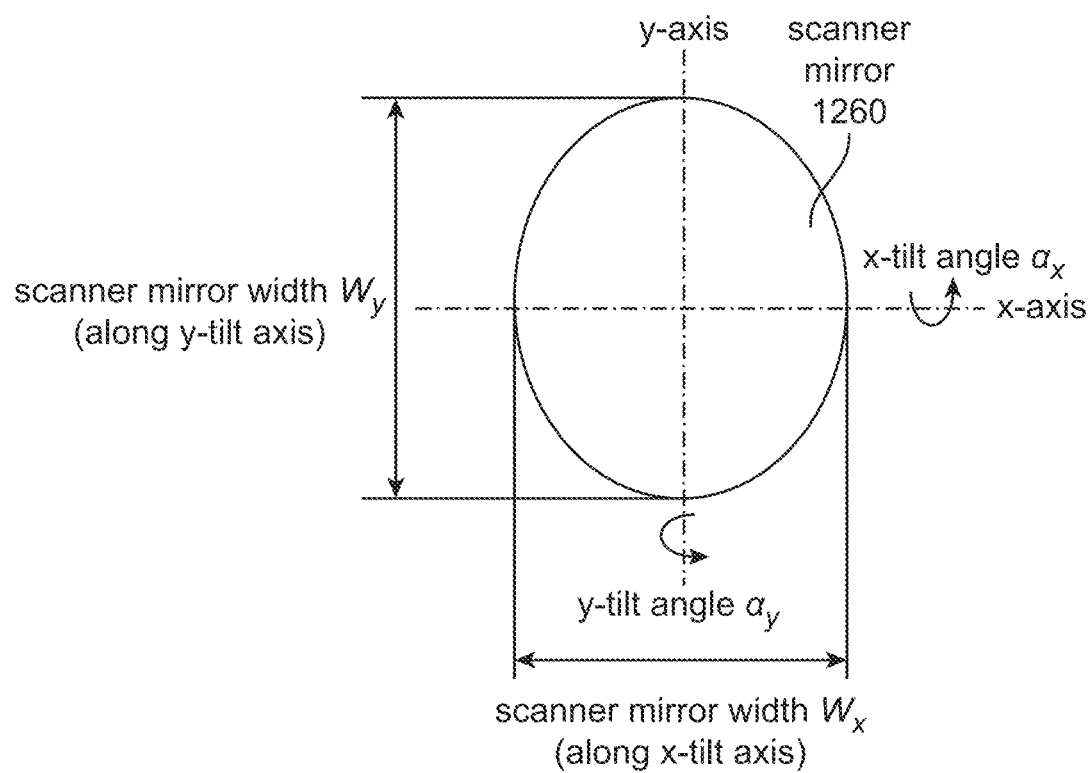
FIG. 12C shows an example of a mirror that may be part of a scanner and used to move a measurement beam on a patient's retina in a scan pattern, in accordance with some embodiments.

FIG. 12C shows an example of a mirror 1260 that may be part of a scanner and used to move a measurement beam on a patient's retina in a scan pattern, in accordance with some embodiments. In the example shown, mirror 1260 has a width $W_X$ as measured along or about an X-tilt or rotation axis and a width $W_Y$ as measured along or about a Y-tilt or rotation axis. Mirror 1260 may be rotated by a tilt angle $\alpha_X$ about the X-axis and rotated by a tilt angle $\alpha_Y$ about the Y-axis. During operation of the OCT system, a drive signal or waveform (or waveforms) is input to a scanner. The drive signal operates to cause an actuator or actuators to move mirror 1260. This may be accomplished by causing the mirror to rotate about the X and/or Y-axes. As the mirror is moved, a measurement beam that reflects off the mirror is redirected and caused to move on a patient's retina in accordance with a scan pattern that is determined by the input drive signal or signals. The light reflected from the surface or internal layers of the retina interferes with a reference version of the measurement beam to form an interferogram which is detected by a detector. Thus, a drive signal to one or more actuators may be varied to cause a measurement beam to be scanned on a retina in a desired scan pattern, with the data detected and stored by other elements of the OCT system.

The mirror 1260 can be configured to scan with a suitable pattern in relation to the drive frequencies associated with the scan pattern, the sampling frequency of A-scans and the resonance frequencies of the scanner. In some embodiments, MEMS electrostatic scanner comprises mirror 1260 configured to pivot about a first pivot axis and a second pivot axis transverse to the first pivot axis to move the measurement beam along the scan pattern. In some embodiments, the processor is configured with instructions that cause the OCT system to perform a measurement of each of the plurality of lobes with a frequency within a range from about 30 Hz to about 120 Hz, and the first axis and the second axis each comprise a resonance frequency within a range from 80 Hz to 700 Hz. In some embodiments, the scanner comprises a first resonance frequency for rotation of the mirror about the first pivot axis and a second resonance frequency for rotation of the mirror about the second pivot axis, in which the first resonance frequency differs from the second resonance frequency by at least about 25%.

The electrostatic MEMS electrostatic scanner may comprise any suitable electrostatic scanner, such as an electrostatic scanner commercially available from Sercalo Microtechnology Limited of Neuchâtel, Switzerland.

Returning to FIG. 12A, each dot along the trajectory of a lobe represents a location where A-scan data is generated and collected by the system. This may be the result of the light source being swept during the scan pattern to generate a plurality of A-scans along the trajectory of the scan pattern. In some embodiments, at least 100 A-scans are generated along the scan pattern. In some embodiments, the number of A-scans along the scan pattern is within a range from about 1000 to 4000 A-scans, for example about 2000 A-scans for a single scan pattern. Each scan pattern can be repeated a suitable number of times, for example repeated from 5 to 20 times, so as to provide an appropriate number of A-scans, for example a number of A-scans within a range from about 5000 to about 80,000, for example about 20,000 A-scans. In some embodiments, the light source is turned on an off while the mirror moves continuously to move the measurement beam in the trajectory along the scan pattern, although the light source may remain on and continuously sweep the wavelengths of the swept source laser to generate the A-scan samples. In some embodiments, a signal to sweep the wavelength of light source may be used to generate data at the desired locations and density of measured A-scan data points along the scan pattern.

In some embodiments, the A-scans are measured at a substantially fixed frequency within a range from about 5 kHz to about 40 kHz, for example within a range from about 5 kHz to about 20 kHz, and the variable distance between A-scan samples provided by varying a velocity of the mirror to vary the velocity of the measurement beam along the scan pattern.

In another example, the light source may be turned on so that data is generated, but the data may only be sampled at certain times by the detector, with the times corresponding to certain locations along the scan pattern. In yet another embodiment, a combination of the light source or measurement beam being turned on and off and swept with a variable sampling rate may be used as the measurement beam moves along the scan pattern.

Each tracing of the measurement beam over a scan pattern generates a plurality of A-scans of a retina, for example at least 100 A-scans in some embodiments. Each A-scan is an interferogram generated by the OCT system for one cycle of the swept source laser such as a VCSEL as described herein. A scan pattern may be repeated multiple times, with each repeated scan pattern generating a plurality of A-scans along each repeated scan pattern. Each scan pattern may be associated with a length of the measurement beam path along a length of the pattern so that each of the plurality of scan patterns has a total length, e.g., the sum of the lengths for each of the individual A-scans along the retina and optionally also the sum of lengths between adjacent non-overlapping A-scans along the retina. Each scan pattern may also be associated with a time period over which the scan is conducted, i.e., a time period over which the measurement beam moves along the pattern of a scan for a single cycle of the scan pattern.

Figure 13:
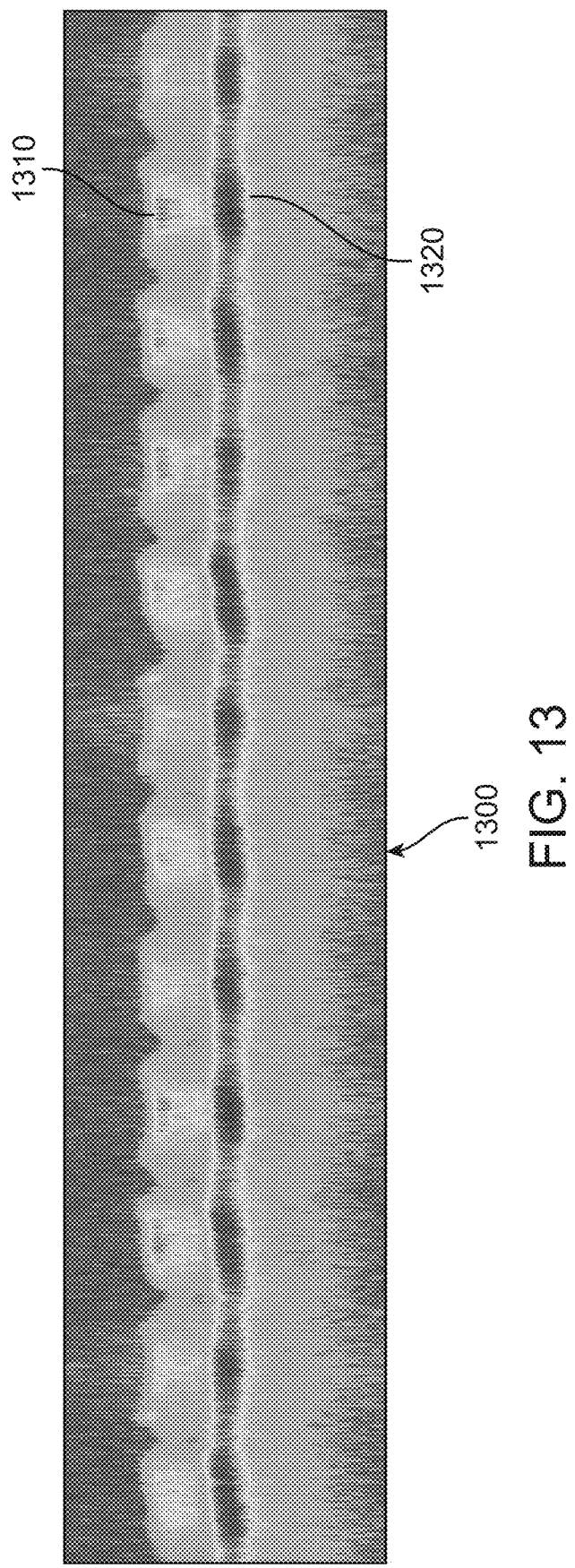
FIG. 13 shows a plurality of A-scans acquired by an OCT device using the scan pattern or trajectory of FIG. 12A, in accordance with some embodiments.

FIG. 13 shows a set of A-scans 1300 acquired by an OCT using the scan pattern of FIG. 12A, in accordance with some embodiments. In the figure, a set of A-scans have been stacked on top of each other in to generate the image shown. In some embodiments, each A-scan is generated by measuring an intensity of an interferogram as the one or more VCSELs is swept in wavelength over time, and Fourier transforming the measured interferogram. In this figure a set of Fourier transformed interferograms is shown, in which each Fourier transformed interferogram corresponds to an A-scan. Each A-scan of the measurement beam along the scan pattern generates one horizontal row of pixels in the figure. Thus, each row of pixels corresponds to one A-scan along the scan pattern.

The OCT system is able to image different depths of the retina and its associated tissue structures. For example, the figure shows an image of the inner limiting membrane (ILM) 1310 and the Retinal Pigment Epithelium (RPE) 1320 obtained by concatenating or stacking multiple scans performed during a cycle of the scan pattern of FIG. 12A.

Figure 14:
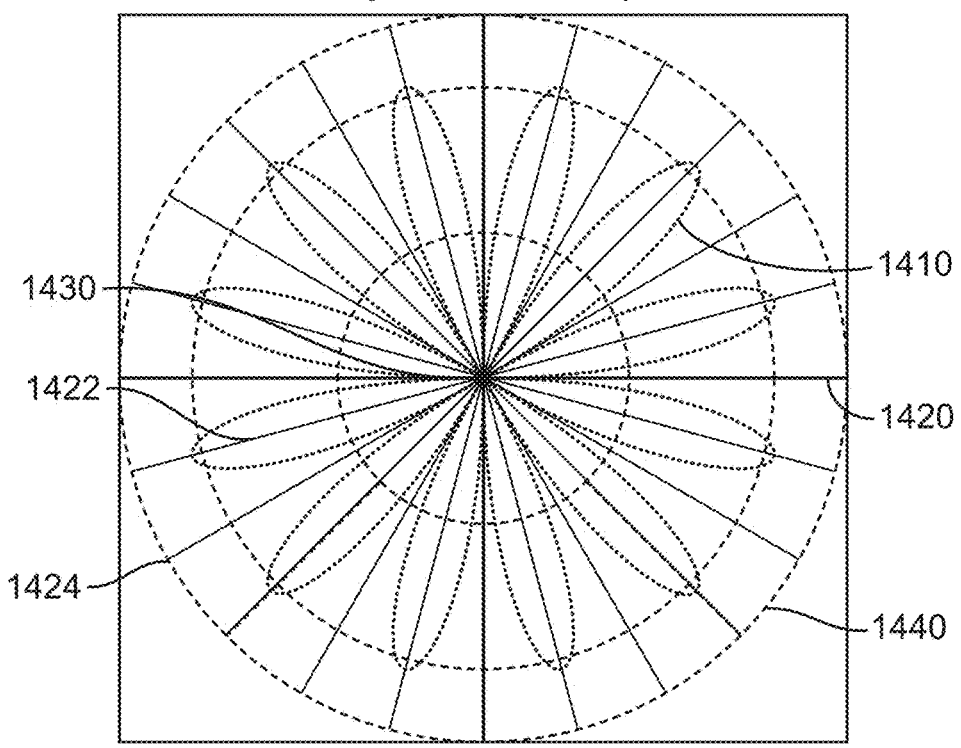
FIG. 14 shows the scan pattern of FIG. 12A superimposed on a radial scan pattern, data for which may be obtained by interpolation of the data obtained from the scan pattern of FIG. 12A, in accordance with some embodiments.

In some embodiments, the data collected may be subjected to further processing to enhance the detectability of a specific medical condition. In some embodiments, this may involve interpolating measurement data acquired as a result of the scan pattern of FIG. 12A to produce data that would be expected to be acquired as a result of a second and different scan pattern. As an example, FIG. 14 shows the scan pattern of FIG. 12A superimposed on a radial scan pattern, the data for which may be obtained by interpolation of the data obtained from the scan pattern of FIG. 12A, in accordance with some embodiments. In this example, data obtained by movement of a measurement beam along a flower scan pattern 1410 may be interpolated or otherwise processed to produce the data expected by performing a scan over the "star" or radial pattern 1420.

The interpolation, extrapolation or other form of processing used to generate data corresponding to a different scan pattern may be based on any suitable technique or methodology, including but not limited to linear interpolation, polynomial interpolation, nearest neighbor interpolation, or spline interpolation, among others.

The interpolation process may be applied to measurement data obtained from moving a measurement beam over the scan pattern of FIG. 12A to generate a set of measurement data that would have been expected to be generated by using the radial scan pattern 1420 of FIG. 14. Note that this capability can be used for several purposes, such as to permit comparisons of measurement data obtained from the scan pattern of FIG. 12A using a first OCT device to data obtained from a different scan pattern (such as the radial or star pattern 1420) using a second device, as a way of comparing the sensitivity or other performance characteristic of the two devices. Alternatively or in combination, the interpolation can be used to generate measurement data for regions "inside" or between the lobes of the scan pattern of FIG. 12A. In this regard, note that in FIG. 14 a radial line is shown extending from a center 1430 of the pattern to an outer ring or annular region 1440 of the image shown in the figure. The figure shows both (a) radial lines extending from the center to the outer ring within a lobe 1422 and (b) radial lines extending from the center to the outer ring between two lobes 1424. This permits a physician or other medical professional to evaluate measurement data from regions of the retina that were not explicitly covered by the scan pattern, and hence can improve the diagnosis and treatment of eye related diseases. Also, although only a portion of the outer annular region 1440 is covered with each scan pattern, work in relation to the present disclosure suggests that this can be sufficient to generate a map of retinal thickness, for example as described with reference to FIG. 12A.

Although FIG. 14 illustrates a star or radial scan pattern, it should be understood that interpolation, extrapolation or other processing of measurement data obtained by use of a flower or rose curve scan pattern may be used to generate measurement data corresponding to other types of scan patterns, including but not limited to stop and go, circular, star, Lissajous and other patterns.

Figure 15:
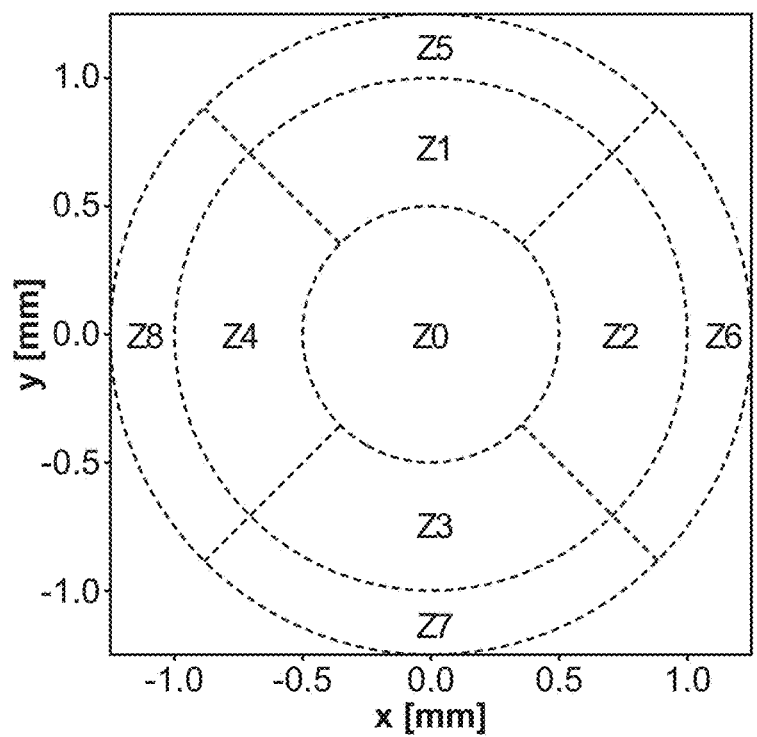
FIG. 15 shows how the fovea and retina near the fovea of a patient's eye may be divided into zones or regions to map retinal thickness, in accordance with some embodiments.

FIG. 15 shows how the retina of a patient's eye may be divided into zones or regions for purposes of comparing scan patterns by comparing the amount of scanning or scan time spent collecting data from each zone, in accordance with some embodiments. As shown in the figure, a surface of an eye may be divided into a set of zones, in this case 9 zones. Each zone is identified by a label Z0, Z1 to Z8 in the figure. In some embodiments, each of the zones can be used to generate a retinal thickness map, in which the overall thickness, e.g. average thickness, for each zone is shown. In some embodiments, data from measurements of the same eye at different times are compared to generate a map showing changes in retinal thickness for each of the zones over time.

In some cases, it may be desirable to compare different scan patterns based on how much scan time and/or data is collected in each zone. This may be useful in selecting a desired scan pattern that causes the collection of measurement data in predominantly one zone or set of zones compared to other zones. This type of analysis may also be used to determine the reliability or confidence of measurement data obtained using one scan pattern from that of another scan pattern, and hence which set of data should be relied upon to better understand the condition of a specific region of the eye.

For example, the Table below shows a percentage of data collected using the flower scan pattern described herein for each of the zones or regions of the eye shown in FIG. 15. As shown in the Table, the central region (or fovea) Z0, is the basis for collecting 32% of the scan data, each of the four regions in the first annular ring (Z1 to Z4) is the source of 13% of the scan data, and each of the four regions in the second annular ring (Z5 to Z8) is the source of 4% of the scan data. Using the flower scan pattern, the central area (or fovea) Z0 is the source of more A-scans than the less important periphery (zones Z5 to Z8). This allows a comparison between different scan patterns with regard to the amount of scan data or number of scans that collect scan data for each of the regions of an eye. Based on this type of comparison, the effectiveness of different scan patterns at collecting data of interest can be determined and may be a factor in deciding which pattern or OCT device to use for a specific patient.

| Zone | Z0 | Z1 | Z2 | Z3 | Z4 | Z5 | Z6 | Z7 | Z8 |
|---|---|---|---|---|---|---|---|---|---|
| Data Collected in Zone | 32% | 13% | 13% | 13% | 13% | 4% | 4% | 4% | 4% |

Figure 16:
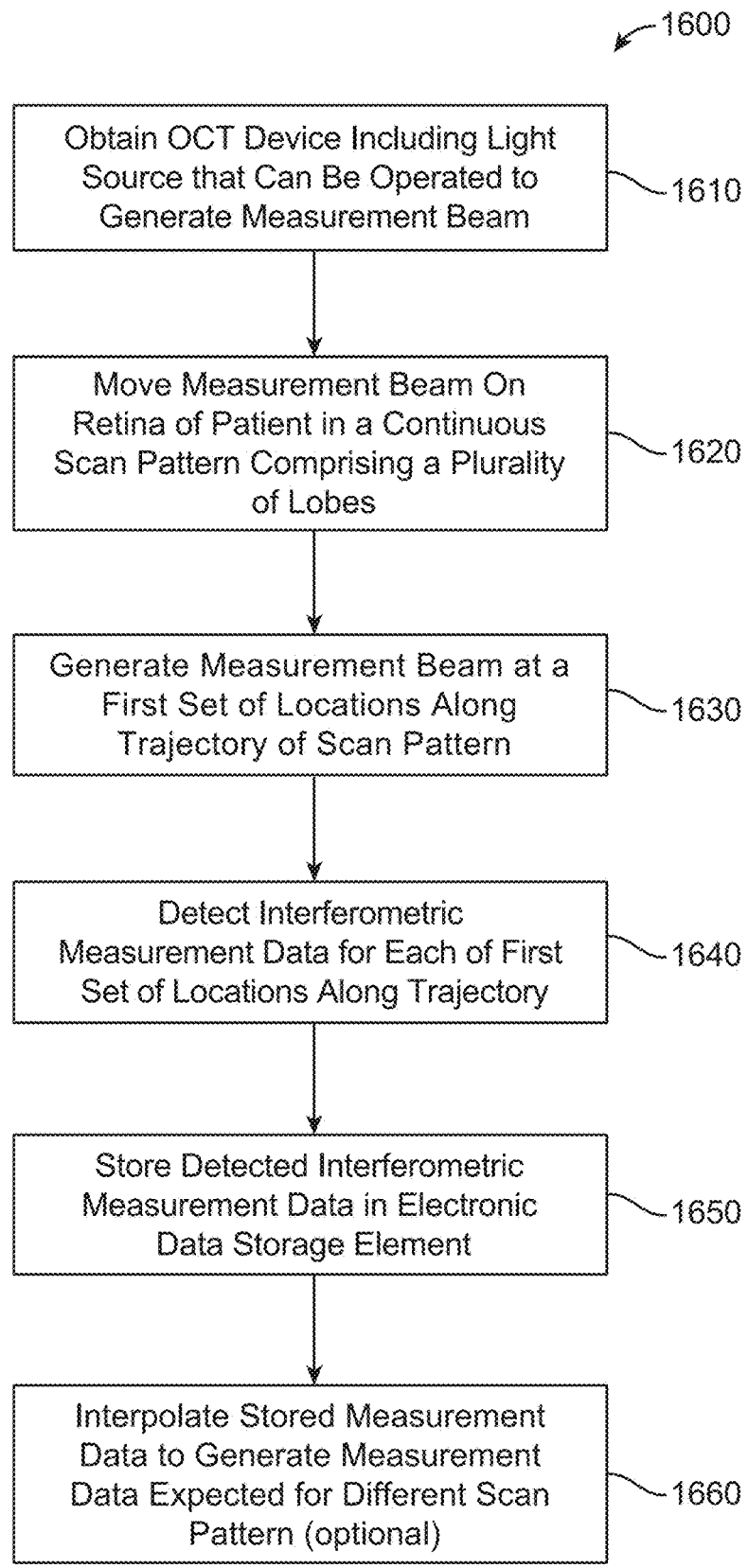
FIG. 16 is a flow chart or flow diagram illustrating a process, method, operation, or function for performing a scan of a patient's retina and generating OCT measurement data, in accordance with some embodiments.

FIG. 16 is a flow chart or flow diagram illustrating a process, method, operation, or function 1600 for performing a scan of a patient's retina and generating OCT measurement data, in accordance with some embodiments. The steps or stages shown in the figure may be performed in whole or in part as a result of the execution of a set of instructions by a programmed processor or processing unit. For example, in some embodiments, execution of the set of instructions will cause the processor to send control signals to turn on and off a light source and also control signals that operate to move a mirror to cause a measurement beam to traverse a trajectory or scan pattern on a patient's retina.

As shown in the figure, with a step or stage 1610, an OCT device is obtained, where the device includes a light source that can be operated to generate a measurement beam. As described, in some embodiments the light source may be a VCSEL that can generate a swept light of varying wavelength. With step or stage 1620, a measurement beam is moved on a patient's retina in a substantially continuous scan pattern, where the scan pattern comprises a plurality of lobes. The mirror is moved substantially continuously during the scan pattern to move the measurement beam over the scan pattern. The measurement beam is swept at a frequency to generate a plurality of A-scan samples along the pattern, as indicated by step or stage 1630. Thus, in some embodiments, the measurement beam is providing light and generating interferometric data at a plurality of locations along the scan pattern. In some embodiments, the sampling occurs at a substantially fixed sampling rate, for example a substantially fixed sampling rate within a range from 10 kHz to 40 kHz. In some embodiments, the points may be selected to correspond to desired locations along the pattern, for example with a variable A-scan sampling rate.

The interferometric data is generated when the swept source generates an A-scan measurement at the locations along scan pattern. At step or stage 1640, this data is detected by a detector that is part of the OCT device. At step or stage 1650, the detected data is stored in an electronic data storage element. Optionally, and as described herein, the stored data collected for one set of points may be interpolated, extrapolated or otherwise processed at step or stage 1660 to generate a set of measurement data that would be generated by measurements made for a different scan pattern. This permits the use of data collected as a result of a first scan pattern (such as the flower pattern) to be used to generate a set of data that would be expected to result from moving the measurement beam over a second scan pattern (for example, a star or radial pattern). This may enable a physician or medical professional to gain greater insight into the condition of a patient's retina and assist in diagnosing or treating the patient.

The OCT system and device described herein may be operated or implemented in accordance with a variety of parameters, settings, programmed configurations, etc. The example operating parameters or characteristics, or range of parameters provided herein are intended to provide guidance to practicing the system and device (or to implementing the process or methods described) and are not meant to provide limits on operational characteristics. As will be apparent to one of skill, other combinations or values of operating parameters or characteristics are possible and are included within the description provided in this disclosure.

As an example, in some embodiments, the scan pattern is a flower pattern or rose curve and has a plurality of lobes. In some embodiments, the number of lobes may vary between four (4) and twenty-four (24). In some embodiments, a scan may be repeated by the device between two (2) and twenty (20) times to collect data.

In some embodiments, a measurement beam path of the scan pattern for a single scan extends a distance within a range from 10 mm to 100 mm, and optionally from 12 mm to 60 mm, for example within a range from about 15 mm to about 50 mm, e.g. about 25 mm. In some embodiments, a total measurement beam path of the scan pattern repeated the plurality of times extends a total combined distance within a range from 100 mm to 1000 mm, and optionally from 120 mm to 600 mm, for example within a range from about 130 mm to about 520 mm, e.g. about 260 mm. In some embodiments, a total time of the scan pattern repeated the plurality of times is within a range from 1 to 3 seconds, and optionally within a range from 1.5 seconds to 2.5 seconds. In some embodiments, the scanner comprises one or more actuators for altering a position of the mirror to move the measurement beam on the retina. In some embodiments, a velocity of the measurement beam moving along the trajectory during a scan is within a range from 10 mm/s to 400 mm/s, and optionally from 15 mm/s to 300 mm/s. In some embodiments, a processor is configured with instructions to generate a plurality of A-scans of the retina with each A-scan comprising the scanner moving the measurement beam along each of the plurality of lobes of a scan pattern, and wherein a sampling rate of the A-scans is within a range from 10 kHz to 50 kHz, and optionally within a range from 15 kHz to 25 kHz.

As used herein, the terms "patient" and "user" are used interchangeably.

As used herein, the terms "OCT device" and "OCT system" are used interchangeably.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. An optical coherence tomography (OCT) system to measure a retina of an eye, comprising: an OCT interferometer comprising a light source to generate a measurement beam, a scanner for moving the measurement beam on the retina in a scan pattern, a plurality of optical elements, and a detector; and a processor operatively coupled to the scanner and configured to execute instructions to cause the scanner to move the measurement beam on the retina in the scan pattern, wherein the scan pattern comprises a plurality of lobes.

Clause 2. The OCT system of clause 1, wherein the scan pattern is defined with a trajectory of a continuously moving measurement beam.

Clause 3. The OCT system of clause 1, wherein the scan pattern comprises a substantially continuous pattern and the measurement beam is turned on and off while the scanner moves the measurement beam.

Clause 4. The OCT system of clause 1, wherein the scan pattern comprises a sinusoid.

Clause 5. The OCT system of clause 3, wherein the scan pattern comprises a rose curve.

Clause 6. The OCT system of clause 3 wherein said scan pattern comprises lobes corresponding to a radial scan.

Clause 7. The OCT system of clause 1, wherein each of the plurality of lobes defines an unscanned internal area located within a scan path of the measurement beam.

Clause 8. The OCT system of clause 1, wherein the scanner comprises a mirror pivoting about a first axis and about a second axis to move the measurement beam along the scan pattern.

Clause 9. The OCT system of clause 6, wherein each of the plurality of lobes comprises a tip oriented away from the first axis and the second axis.

Clause 10. The OCT system of clause 1, wherein the scan pattern includes between four (4) and twenty-four (24) lobes.

Clause 11. The OCT system of clause 1, wherein the processor is configured with instructions to generate a plurality of A-scans of the retina with each A-scan comprising the scanner moving the measurement beam along each of the plurality of lobes of a scan pattern, and wherein a sampling rate of the A-scans is within a range from 10 kHz to 50 kHz, and optionally within a range from 15 kHz to 25 kHz.

Clause 12. The OCT system of clause 1, wherein the set of instructions further comprises instructions to repeat the scan pattern between two (2) and twenty (20) times to collect measurement data.

Clause 13. The OCT system of clause 1, further comprising instructions to cause the processor to process measurement data to perform an interpolation of data obtained as the measurement beam moves on the retina.

Clause 14. The OCT system of clause 11, wherein the interpolation produces a set of measurement data that corresponds to a scan pattern comprising a plurality of substantially straight lines extending radially from a center of the scan pattern.

Clause 15. The OCT system of clause 12, wherein the interpolation produces a set of measurement data that corresponds to a scan pattern comprising a straight line extending radially from the center of the scan pattern with a line centered within each lobe of the plurality of lobes.

Clause 16. The OCT system of clause 13, further comprising measurement data that corresponds to a scan pattern comprising a straight line extending radially from the center of the scan pattern with a line centered between each lobe of the plurality of lobes.

Clause 17. The OCT system of clause 1, wherein a measurement beam path of the scan pattern for a single scan extends a distance within a range from 10 mm to 100 mm, and optionally from 12 mm to 60 mm.

Clause 18. The OCT system of clause 10, wherein a total measurement beam path of the scan pattern repeated for the plurality of times extends a total distance within a range from 100 mm to 1000 mm, and optionally from 120 mm to 600 mm.

Clause 19. The OCT system of clause 10, wherein a total time of the scan pattern repeated the plurality of times is within a range from 1 to 3 seconds, and optionally within a range from 1.5 seconds to 2.5 seconds.

Clause 20. The OCT system of clause 6, wherein the scanner comprises one or more actuators for altering a position of the mirror to move the measurement beam on the retina.

Clause 21. The OCT system of clause 1, wherein a velocity of the measurement beam moving along the trajectory during a scan is within a range from 10 mm/s to 400 mm/s, and optionally from 15 mm/s to 300 mm/s.

Clause 22. The OCT system of clause 18, wherein the position of the mirror is altered by the application of an electrostatic force.

Clause 23. The OCT system of clause 20, wherein the electrostatic force is applied to the mirror by a plurality of microelectromechanical-system (MEMS) elements.

Clause 24. The OCT system of clause 21, wherein the microelectromechanical-system (MEMS) elements comprise a plurality of capacitors.

Clause 25. The OCT system of clause 18, wherein the position of the mirror is altered by the application of an electromagnetic force.

Clause 26. The OCT system of clause 23, wherein the position of the mirror is altered by one or more of a galvanometer, an electrostatic transducer, or a piezo electric transducer.

Clause 27. The OCT system of clause 1, wherein the light source comprises a swept light source configured to vary an emitted wavelength.

Clause 28. The OCT system of clause 25, wherein the swept light source comprises a vertical cavity surface emitting laser (VCSEL).

Clause 29. The OCT system of clause 25, wherein the emitted wavelength varies in response to one or more of heating, a change of index, or an increase of length of a laser gain medium.

Clause 30. The OCT system of clause 26, wherein the VCSEL comprises a laser cavity with a substantially fixed distance between mirrors of a cavity.

Clause 31. The OCT system of clause 25, wherein the emitted wavelength varies by an amount within a range from 5 nm to 20 nm, and optionally within a range from 6 nm to 10 nm.

Clause 32. The OCT system of clause 2, wherein each time the measurement beam is turned on a sample of measurement data is generated and detected by the detector.

Clause 33. The OCT system of clause 30, wherein the number of samples of measurement data generated varies along different portions of the trajectory of the scan pattern.

Clause 34. The OCT system of clause 31, wherein the number of samples of measurement data generated is increased along a portion of the trajectory at a tip of each lobe of the plurality of lobes, wherein the tip of each lobe is a region of the lobe opposite a center of the scan pattern.

Clause 35. The OCT system of clause 31, wherein the generated samples of data along the trajectory of the scan pattern comprises overlapping samples along a first portion of the trajectory and non-overlapping samples along a second portion of the trajectory.

Clause 36. The OCT system of clause 6, wherein the scanner has a resonant frequency and receives as an input a first drive signal for altering the position of the mirror with respect to the first axis and a second drive signal for altering the position of the mirror with respect to the second axis, wherein the first and second drive signals comprise frequencies less than the resonant frequency, and optionally wherein the first and second drive signals comprise a maximum frequency less than the resonance frequency of the scanner.

Clause 37. The OCT system of clause 1, wherein the processor is configured to execute instructions to cause the scanner to move the measurement beam on the retina along the scan pattern to generate a plurality of A-scans of the retina, the plurality of A-scans comprising data corresponding to a retinal pigment epithelium (RPE) and an inner limiting membrane (ILM) of the retina.

Clause 38. The OCT system of clause 1, wherein the scanner comprises a mirror configured to pivot about a first pivot axis and a second pivot axis transverse to the first pivot axis to move the measurement beam along the scan pattern.

Clause 39. The OCT system of clause 36, wherein the processor is configured with instructions measure each of the plurality of lobes with a frequency within a range from about 30 Hz to about 120 Hz and wherein the first axis and the second axis each comprise a resonance frequency within a range from 80 Hz to 700 Hz.

Clause 40. The OCT system of clause 36, wherein the scanner comprises a first resonance frequency for rotation of the mirror about the first pivot axis and a second resonance frequency for rotation of the mirror about the second pivot axis, the first resonance frequency different from the second resonance frequency by at least about 25%.

Clause 41. A method for performing optical coherence tomography (OCT) to measure a retina of an eye, comprising: operating a source of light to generate a measurement beam; moving the measurement beam on the retina in a scan pattern, the scan pattern comprising a plurality of lobes; generating the measurement beam at a plurality of locations along the scan pattern; detecting a sample of interferometric measurement data by a detector for each of the plurality of locations; and storing the detected samples of interferometric measurement data for each of the locations in an electronic data storage element.

Clause 42. The method of clause 37, wherein the scan pattern is defined with a trajectory of a continuously moving measurement beam.

Clause 43. The method of clause 37, wherein the sample at each of the plurality of locations comprises an A-scan of the retina at the location.

Clause 44. The method of clause 37, wherein the wherein the measurement beam is generated at a first set of locations along the scan pattern and not generated at a second set of locations along the scan pattern.

Clause 45. The method of clause 37, further comprising altering a position of a mirror that intercepts the measurement beam to move the beam on the retina.

Clause 46. The method of clause 37, wherein the scan pattern comprises a rose curve.

Clause 47. The method of clause 37, wherein the scan pattern includes between four (4) and twenty-four (24) lobes.

Clause 48. The method of clause 37, further comprising repeating the scan pattern between two (2) and twenty (20) times to collect measurement data.

Clause 49. The method of clause 37, further comprising applying an electrostatic force to alter the position of the mirror.

Clause 50. The method of clause 37, wherein the mirror is configured to pivot about a first pivot axis and a second pivot axis transverse to the first pivot axis to move the measurement beam along the scan pattern.

Clause 51. The method of clause 44, wherein the electrostatic force is applied to the mirror by a plurality of microelectromechanical-system (MEMS) elements.

Clause 52. The OCT system of clause 46, wherein the microelectromechanical-system (MEMS) elements comprise a plurality of capacitors.

Clause 53. The OCT system of clause 37, wherein a position of the mirror is altered by the application of an electromagnetic force.

Clause 54. The OCT system of clause 48, wherein the position of the mirror is altered by one or more of a galvanometer, an electrostatic transducer, or a piezo electric transducer.

Clause 55. The method of clause 37, further comprising interpolating the detected samples of interferometric measurement data obtained as the measurement beam moves on the retina in a first scan pattern to generate a set of measurement data that would be generated for a second scan pattern.

Clause 56. The method of clause 37, wherein the light source comprises a swept light source configured to vary an emitted wavelength.

Clause 57. The method of clause 51, wherein the swept light source comprises a vertical cavity surface emitting laser (VCSEL).

Clause 58. The method of clause 37, wherein each time the measurement beam is generated, a sample of measurement data is generated and detected by the detector.

Clause 59. The method of clause 53, wherein the number of samples of measurement data generated varies along different portions of the trajectory of the scan pattern.

Clause 60. The method of clause 54, wherein the number of samples of measurement data generated is increased along a portion of the trajectory at a tip of each lobe of the plurality of lobes, wherein the tip of each lobe is a region of the lobe opposite a center of the scan pattern.

Clause 61. The method of clause 37, further comprising applying a first drive signal to alter the position of the mirror with respect to a first axis and applying a second drive signal to alter the position of the mirror with respect to a second axis, wherein the first and second drive signals comprise frequencies less than a resonant frequency of a device used to perform OCT, and optionally wherein the first and second drive signals comprise a maximum frequency less than the resonance frequency of the device.

Clause 62. The method of clause 37, wherein one or more mirrors of the scanner move continuously with one or more rotations corresponding to a trajectory of the scan pattern and a swept source VCSEL turns on and off with a frequency in relation to a size of the beam and a velocity of the beam on the retina such that a plurality of A-scans of the measurement beam overlap.

Clause 63. The OCT system of clause 1, wherein a mirror of the scanner moves continuously with one or more rotations corresponding to a trajectory of the scan pattern and a swept source VCSEL turns on and off with a frequency in relation to a size of the beam and a velocity of the beam on the retina such that a plurality of A-scans of the measurement beam overlap.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An optical coherence tomography (OCT) system to measure a retina of an eye, comprising:
    an OCT interferometer comprising a light source to generate a measurement beam, a scanner for moving the measurement beam on the retina in a scan pattern, a plurality of optical elements, and a detector; and
    a processor operatively coupled to the scanner and configured to execute instructions to cause the scanner to move the measurement beam on the retina in the scan pattern, wherein the scanner comprises a mirror configured to pivot about a first pivot axis and a second pivot axis transverse to the first pivot axis to move the measurement beam along the scan pattern, wherein the scan pattern comprises a plurality of lobes, wherein a total measurement beam path of the scan pattern repeated for a plurality of times extends a total distance within a range from 100 mm to 1000 mm, wherein the scanner comprises a first resonance frequency for rotation of the mirror about the first pivot axis and a second resonance frequency for rotation of the mirror about the second pivot axis, the first resonance frequency different from the second resonance frequency by at least about 25%.

2. The OCT system of claim 1, wherein the scan pattern comprises a rose curve.

3. The OCT system of claim 1, wherein said scan pattern comprises lobes corresponding to a radial scan.

4. The OCT system of claim 1, wherein the scanner comprises a mirror pivoting about a first axis and about a second axis to move the measurement beam along the scan pattern.

5. The OCT system of claim 1, wherein the scan pattern includes between four (4) and twenty-four (24) lobes.

6. The OCT system of claim 1, wherein the processor is configured with instructions to generate a plurality of A-scans of the retina with each A-scan comprising the scanner moving the measurement beam along each of the plurality of lobes of the scan pattern, and wherein a sampling rate of the A-scans is within a range from 10 kHz to 50 kHz.

7. The OCT system of claim 1, wherein a measurement beam path of the scan pattern for a single scan extends a distance within a range from 10 mm to 100 mm.

8. The OCT system of claim 5, wherein the total measurement beam path of the scan pattern repeated for the plurality of times extends a total distance within a range from 120 mm to 600 mm.

9. The OCT system of claim 4, wherein a position of the mirror is altered by the application of an electrostatic force.

10. The OCT system of claim 1, wherein the light source comprises a swept light source configured to vary an emitted wavelength.

11. The OCT system of claim 10, wherein the swept light source comprises a vertical cavity surface emitting laser (VCSEL).

12. The OCT system of claim 8, wherein an emitted wavelength varies in response to one or more of heating, a change of index, or an increase of length of a laser gain medium.

13. The OCT system of claim 1, wherein the processor is configured to execute instructions to cause the scanner to move the measurement beam on the retina along the scan pattern to generate a plurality of A-scans of the retina, the plurality of A-scans comprising data corresponding to a retinal pigment epithelium (RPE) and an inner limiting membrane (ILM) of the retina.

14. The OCT system of claim 1, wherein the mirror of the scanner moves continuously with one or more rotations corresponding to a trajectory of the scan pattern and a swept source VCSEL turns on and off with a frequency in relation to a size of the measurement beam and a velocity of the measurement beam on the retina such that a plurality of A-scans of the measurement beam overlap.

\* \* \* \* \*